US008067553B2

(12) United States Patent
Williams et al.

(10) Patent No.: US 8,067,553 B2
(45) Date of Patent: Nov. 29, 2011

(54) PEG-URATE OXIDASE CONJUGATES AND USE THEREOF

(75) Inventors: L. David Williams, Fremont, CA (US); Michael S. Hershfield, Durham, NC (US); Susan J. Kelly, Chapel Hill, NC (US); Mark G. P. Saifer, San Carlos, CA (US); Merry R. Sherman, San Carlos, CA (US)

(73) Assignees: Mountain View Pharmaceuticals, Inc., Menlo Park, CA (US); Duke University, Durham, NC (US)

( * ) Notice: Subject to any disclaimer, the term of this patent is extended or adjusted under 35 U.S.C. 154(b) by 0 days.

(21) Appl. No.: 12/769,570

(22) Filed: Apr. 28, 2010

(65) Prior Publication Data
US 2010/0323422 A1 Dec. 23, 2010

Related U.S. Application Data

(62) Division of application No. 09/839,946, filed on Apr. 19, 2001, now Pat. No. 7,723,089, which is a division of application No. 09/370,084, filed on Aug. 6, 1999, now Pat. No. 6,576,235.

(60) Provisional application No. 60/219,318, filed on Aug. 6, 1998, now abandoned.

(51) Int. Cl.
*A23J 1/00* (2006.01)
(52) U.S. Cl. ......... 530/412; 435/189; 435/190; 435/191
(58) Field of Classification Search .................. 530/412; 435/189, 190, 191
See application file for complete search history.

(56) References Cited

U.S. PATENT DOCUMENTS

| 3,616,231 | A | 10/1971 | Bergmeyer et al. |
| 4,179,337 | A | 12/1979 | Davis et al. |
| 4,460,683 | A | 7/1984 | Gloger et al. |
| 4,766,106 | A | 8/1988 | Katre et al. |
| 4,847,079 | A | 7/1989 | Kwan |
| 4,847,325 | A | 7/1989 | Shadle et al. |
| 4,917,888 | A | 4/1990 | Katre et al. |
| 5,122,614 | A | 6/1992 | Zalipsky |
| 5,283,317 | A | 2/1994 | Saifer et al. |
| 5,286,637 | A | 2/1994 | Veronese et al. |
| 5,428,128 | A | 6/1995 | Mensi-Fattohi et al. |
| 5,458,135 | A | 10/1995 | Patton et al. |
| 5,468,478 | A | 11/1995 | Saifer et al. |
| 5,541,098 | A | 7/1996 | Caput et al. |
| 5,612,460 | A | 3/1997 | Zalipsky |
| 5,643,575 | A | 7/1997 | Martinez et al. |
| 5,653,974 | A | 8/1997 | Hung et al. |
| 5,711,944 | A | 1/1998 | Gilbert et al. |
| 5,762,923 | A | 6/1998 | Gross et al. |
| 5,811,096 | A | 9/1998 | Aleman et al. |
| 5,824,784 | A | 10/1998 | Kinstler et al. |
| 5,880,255 | A | 3/1999 | Delgado et al. |
| 5,919,455 | A | 7/1999 | Greenwald et al. |
| 5,932,462 | A | 8/1999 | Harris et al. |
| 5,955,336 | A | 9/1999 | Shigyo et al. |
| 6,201,110 | B1 | 3/2001 | Olsen et al. |
| 6,576,235 | B1 | 6/2003 | Williams et al. |
| 6,783,965 | B1 | 8/2004 | Sherman et al. |
| 6,913,915 | B2 | 7/2005 | Ensor et al. |
| 7,723,089 | B2 | 5/2010 | Williams et al. |
| 2002/0010319 | A1 | 1/2002 | Ansaldi et al. |
| 2003/0166249 | A1 | 9/2003 | Williams et al. |
| 2005/0014240 | A1 | 1/2005 | Sherman et al. |
| 2008/0031864 | A1 | 2/2008 | Williams et al. |
| 2008/0057048 | A1 | 3/2008 | Sherman et al. |
| 2010/0323423 | A1 | 12/2010 | Williams et al. |

FOREIGN PATENT DOCUMENTS

| DE | 279 486 A1 | 6/1990 |
| EP | 0 043 980 A2 | 1/1982 |
| JP | 55-99189 A | 7/1980 |
| JP | 55-135590 A | 10/1980 |
| JP | 57-192435 A | 11/1982 |
| JP | 62-55079 A | 3/1987 |
| JP | 03-148298 A | 6/1991 |
| JP | 09-154581 A | 6/1997 |
| WO | WO 87/00056 A1 | 1/1987 |
| WO | WO 92/16221 A1 | 10/1992 |
| WO | WO 94/19007 A1 | 9/1994 |
| WO | WO 94/23740 A1 | 10/1994 |
| WO | WO 98/31383 A1 | 7/1998 |
| WO | WO 00/07629 A2 | 2/2000 |
| WO | WO 00/08196 A3 | 2/2000 |
| WO | WO 01/59078 A2 | 8/2001 |

OTHER PUBLICATIONS

Osman et al. [Comp. Biochem. Physiol. vol. 94B, No. 3, pp. 469-474 (1989)].*
Kunitani et al. [Journal of Pharmaceutical and Biomedical Analysis, vol. 16, pp. 573-586 (1997)].*
Abuchowski, A., et al., "Effect of Covalent Attachment of Polyethylene Glycol on Immunogenicity and Circulating Life of Bovine Liver Catalase," *J. Biol. Chem. 252*:3582-3586, American Society for Biochemistry and Molecular Biology, United States (1977).
Abuchowski, A., et al., "Reduction of Plasma Urate Levels in the Cockerel with Polyethylene Glycol-Uricase," *J. Pharmacol. Exp. Ther. 219*: 352-354, The American Society for Pharmacology and Experimental Therapeutics, United States (1981).
Alvares, K., et al., "Rat urate oxidase produced by recombinant baculovirus expression: formation of peroxisome crystalloid corelike structures," *Proc. Natl. Acad. Sci. USA 89*: 4908-4912, National Academy of Sciences, United States (1992).
Alvares, K., et al., "The Nucleotide Sequence of a Full Length cDNA Clone Encoding Rat Liver Urate Oxidase," *Biochem. Biophys. Res. Commun. 158*:991-995, Academic Press, Inc., United States (1989).
Bossavy, J., et al., "Comparison of the Antithrombotic Effect of PEG-Hirudin and Heparin in a Human Ex Vivo Model of Arterial Thrombosis," *Arterioscler. Thromb. Vasc. Biol. 19* :1348-1353, American Heart Association, United States (May 1999).

(Continued)

*Primary Examiner* — Tekchand Saidha
(74) *Attorney, Agent, or Firm* — Sterne, Kessler, Goldstein & Fox PLLC

(57) ABSTRACT

A naturally occurring or recombinant urate oxidase (uricase) covalently coupled to poly(ethylene glycol) or poly(ethylene oxide) (both referred to as PEG), wherein an average of 2 to 10 strands of PEG are conjugated to each uricase subunit and the PEG has an average molecular weight between about 5 kDa and 100 kDa. The resulting PEG-uricase conjugates are substantially non-immunogenic and retain at least 75% of the uricolytic activity of the unmodified enzyme.

6 Claims, 17 Drawing Sheets

OTHER PUBLICATIONS

Braun, A. and J. Alsenz, "Development and Use of Enzyme-Linked Immunosorbent Assays (ELISA) for the Detection of Protein Aggregates in Interferon-Alpha (IFN-α) Formulations," *Pharm. Res.* 14:1394-1400, Plenum Publishing Corporation, United States (Oct. 1997).

Braun, A., et al., "Protein Aggregates Seem to Play a Key Role Among the Parameters Influencing the Antigenicity of Interferon Alpha(IFN-α) in Normal and Transgenic Mice," *Pharm. Res.* 14:1472-1478, Plenum Publishing Corporation, United States (Oct. 1997).

Burnham, N., "Polymers for delivering peptides and proteins," *Am. J. Hosp. Pharm. 51*: 210-218, American Society of Hospital Pharmacists, Inc., United States (1994).

Caliceti, P., et al., "Biopharmaceutical properties of uricase conjugated to neutral and amphiphilic polymer," *Bioconjugate Chem.* 10:638-646, American Chemical Society, United States (Jun. 1999).

Chen, R., et al., "Properties of Two Urate Oxidases Modified by the Covalent Attachment of Poly(Ethylene Glycol)," *Biochim. Biophys. Acta 660*:293-298, Elsevier/North Holland Biomedical Press, Netherlands (1981).

Chua, C., et al., "Use of Polyethylene Glycol-Modified Uricase (PEG-Uricase) to Treat Hyperuricemia in a Patient with Non-Hodgkin Lymphoma," *Ann. Intern. Med. 109*:114-117, American College of Phsycians, United States (1988).

Clark, R., et al., "Long-acting Growth Hormone Produced by Conjugation with Polyethylene Glycol," *J. Biol. Chem.* 271:21969-21977, The American Society of Biochemistry and Molecular Biology, Inc., United States (1996).

Colloc'h, N., et al., "Crystal Structure of the protein drug urate oxidase-inhibitor complex at 2.05 Å resolution," *Nature Struct. Biol.* 4:947-952, Nature Publishing Group, United Kingdom (Nov. 1997).

Conley, T. and D. Priest, "Thermodynamics and Stoichceiometry of the Binding of Substrate Analogues to Uricase," *Biochem. J. 187*:727-732, The Biochemical Society, United Kingdom (1980).

Davis, F., et al., "Enzyme-Polyethylene Glycol Adducts: Modified Enzymes with Unique Properties," in *Enzyme Engineering*, vol. 4, Braun, G., et al., eds, Plenum Press, New York, pp. 169-173 (1978).

Davis, S., et al., "Hypouricaemic Effect of Polyethyleneglycol Modified Urate Oxidase," *Lancet 2*:281-283, Lancet Publishing Group, United States (1981).

Donadio, D., et al., "Manifestation de type anaphylactique après injection intra-veineuse d'urate-oxydase chez un enfant asthmatique atteint de leucémie aiguë," *La Nouv. Presse Med. 10*:711-712, Masson, France (1981) (with English language translation).

Fam, A., "Strategies and Controversies in the Treatment of Gout and Hyperuricaemia," *Ballière's Clinical Rheumatology 4*:177-192, Elsevier, Ltd., United Kingdom (1990).

Francis, G., et al., "PEGylation of cytokines and other therapeutic proteins and peptides: the importance of biological optimisation of coupling techniques," *Int. J. Hematol. 68*:1-18, Elsevier Science Ireland Ltd., Ireland (Jul. 1998).

Fridovich, I., "The Competitive Inhibition of Uricase by Oxonate and by Related Derivatives of s-Triazines," *J. Biol. Chem. 240*:2491-2494, American Society for Biochemistry and Molecular Biology, United States (1965).

Fuertges, F. and A. Abuchowski, "The Clinical Efficacy of Poly(Ethylene Glycol)-Modified Proteins," *J. Control Release 11*: 139-148, Elsevier Science, Netherlands (1990).

Fujita, T., et al., "Tissue Distribtuion of $^{111}$In-Labeled Uricase Conjugated with Charged Dextrans and Polyethylene Glycol," *J. Pharmacobio-Dyn. 14*:623-629, Pharmaceutical Society of Japan, Japan (1991).

Gaertner, H. and R. Offord, "Site-Specific Attachment of Functionalized Poly(ethylene glycol) to the Amino Terminus of Proteins," *Bioconjugate Chem. 7*:38-44, American Chemical Society, United States (1996).

Greenberg, M. and M. Herschfield, "A Radiochemical-High-Performance Liquid Chromatographic Assay for Urate Oxidase in Human Plasma," *Anal. Biochem. 176*:290-293, Academic Press, Inc., United States (1989).

Hande, K., et al., "Severe Allopurinol Toxicity. Description and Guidelines for Prevention in Patients in Renal Insufficiency," *Am. J. Med. 76*:47-56, Excerpta Medica, United States (1984).

Hedlund, L., et al., "Magnetic Resonance Microscopy of Toxic Renal Injury Induced by Bromethylarnine in Rats," *Fundam. Appl. Toxicol. 15*:787-797, Academic Press, United States (1991).

Henney, C. and E. Ellis, "Antibody Production to Aggregated Human γG-Globulin in Acquired Hypogammaglobulinemia," *New Engl. J. Med. 278*:1144-1146, Massachusetts Medical Society, United States (1968).

Herbst, R., et al., "Folding of Firefly (*Photinus pyralis*) Luciferase: Aggregation and Reactivation of Unfolding Intermediates," *Biochem. 37*:6586-6597, American Chemical Society, United States (Apr. 1998).

Herschfield, M., "Biochemistry and Immunology of Poly(ethylene glycol)-Modified Adenosine Deaminase (PEG-ADA)," in *ACS Symposium Series 680. Poly(ethylene glycol). Chemistry and Biological Applications*, Harris, J. and Zalipsky, S., eds., American Chemistry Society, Washington, D.C., pp. 145-154 (Apr. 1997).

Herschfield, M., et al., "Use of Site-Directed Mutagenesis to Enhance the Epitope-shielding Effect of Covalent Modification of Proteins with Polyethylene Glycol," *Proc. Natl. Acad. Sci. USA 88*:7185-7189, National Academy of Sciences, United States (1991).

Hinds, K., et al., "Synthesis and Characterization of poly(ethylene glycol)-insuline conjugates," *Bioconjugate Chem. 11*:195-201, American Chemical Society, United States (Feb. 2000).

Inada, Y., et al., "Biomedical and biotechnological applications of PEG- and PM-modified proteins," *Trends Biotechnol. 13*:86-91, Elsevier Science, Ltd., Netherlands (1995).

Ishino, K. and S. Kudo, "Protein Concentration Dependence on Aggregation Behavior and Properties of Soybean 7S and 11S Globulins during Alkali-treatement," *Agric. Biol. Chem. 44*:1259-1266, Agricultural Chemical Society of Japan, Japan (1980).

Ito, M., et al., "Identification of an Amino Acid Residue Involved in the Substrate-binding Site of Rat Liver Uricase by Site-directed Mutagenesis," *Biochem. Biophys. Res. Commun. 187*:101-107, Academic Press, United States (1992).

Kahn, K. and P. Tipton, "Kinetic Mechanism and Cofactor Content of Soybean Root Nodule Urate Oxidase," *Biochemistry 36*:4731-4738, American Chemical Society, United States (Apr. 1997).

Kelly, S., et al., "Diabetes Insipidus in Uricase-Deficient Mice: A Model for Evaluating Therapy with Poly(Ethylene Glycol)-Modified Uricase," *J. Am. Soc. Nephrol. 12*:1001-1009, Lippincott Williams & Wilkins, United States (May 2001).

Kinstler, O., et al., "Characterization and Stability of N-terminally PEGylated rhG-CSF," *Pharm. Res. 13*:996-1002, Plenum Publishing Corporation, United States (1996).

Kito, M., et al., "A Simple and Efficient Method for Preparation of Monomethoxypolyethylene Glycol Activated with *p*-Nitrophenylchloroformate and Its Application Modification of L-Asparaginase," *J. Clin. Biochem. Nutr. 21*:101-111, Institute of Applied Biochemistry, Japan (1996).

Konstek, et al., "Forty years of interferon," *Acta Virologica 41*:349-353, Slovak Academic Press, Slovak Republic (Oct. 1997).

Kral, L., et al., "Cloning a cDNA for *Drosophila melanogastar* urate oxidase," *Gene 45*:131-137, Elsevier Science Publishers B.V., Netherlands (1986).

Kunitani, M., et al., "On-line characterization of polyethylene glycol-modified proteins," *J. Chromat. 588*:125-137, Elsevier Science Publishers B.V., Netherlands (1991).

Kunitani, M., et al., "Classical light scattering quantitation of protein aggregates: off-line spectroscopy versus HPLC detection," *J. Pharm. Biomed. Anal. 16*:573-586, Elsevier Science B.V., Netherlands (Dec. 1997).

Leach, M., et al., "Efficacy of Urate Oxidase (Uricozyme) in Tumor Lysis Induced Urate Nephropathy," *Clin. Lab. Haematol. 20*:169-172, Blackwell Scientific Publications (Jun. 1998).

Lee, C., et al., "Generation of cDNA Probes Directed by Amino Acid Sequence: Cloning of Urate Oxidase," *Science 239*:1288-1291, American Association for the Advancement of Science, United States (1988).

Legoux, R., et al., "Cloning and Expression in *Eschericia coli* of the Gene Encoding *Aspergillus flavus* Urate Oxidase," *J. Biol. Chem.* 267:8565-8570, American Society for Biochemistry and Molecular Biology, United States (1992).

Mahler, H. et al., "Studies of Uricase. I. Preparation, Purification, and Properties of a Cuproprotein," *J. Biol. Chem.* 216:625-641, American Society for Biochemistry and Molecular Biology, United States (1955).

Mahmoud, H., et al., "Advances in the Management of Malignancy-Associated Hyperuricaemia," *Br. J. Cancer (Supplement 4)*77:18-20, Churchill Livingstone, United Kingdom (Sep. 1998).

Malakhova, E., et al., "Kinetic Properties of Bacterial Urate Oxidase Entrapped in Hydrated Reversed Micelles," *Biologicheskie Membrany* 8:453-459, Nauka, Russia (1991) (with English language abstract).

Miura, S., et al., "Urate Oxidase is Imported into Peroxisomes Recognizing the C-terminal SKL Motif of Proteins," *Eur. J. Biochem.* 223:141-146, Blackwell Science Ltd., United Kingdom (1994).

Monkarsh, et al., "Positional isomers of monopegylated interferon alpha-2a: isolation, characterization, and biological activity," *Anal. Biochem.* 247:434-440, Academic Press, United States (May 1997).

Montalbini, P., et al., "Isolation and characterization of uricase from bean leaves and its comparison with uredospore enzymes," *Plant Sci.* 147:139-147, Elsevier Science Ireland Ltd. (Sep. 1999).

Montalbini, P., et al., "Uricase from leaves: its purification and characterization from three different higher plants," *Planta* 202:277-283, Springer-Verlag, Germany (Jul. 1997).

Moore, W. and P. Leppert, "Role of Aggregated Human Growth Hormone (hGH) in Development of Antibodies to hGH," *J. Clin. Endocrinol. Metab.* 51:691-697, The Endocrine Society, United States (1980).

Motojima, K., et al., "Cloning and sequence analysis of cDNA for rat liver uricase," *J. Biol. Chem.* 263:16677-16681, American Society for Biochemistry and Molecular Biology, United States (1988).

Nishida, Y., et al., "Hypouricaemic effect after oral administration in chickens of polyethylene glycol-modified uricase entrapped in liposomes," *J. Pharm. Pharmacol.* 36:354-355, Pharmaceutical Press, United Kingdom (1984).

Nishimura, H., et al., "Improved Modification of Yeast Uricase with Polyethylene Glycol: Accompanied with Nonimmunoreactivity Towards Anti-Uricase Serum and High Enzyme Activity," *Enzyme* 26:49-53, Karger, Switzerland (1981).

Nishimura, H., et al., "Modification of Yeast Uricase with Polyethylene Glycol: Disappearance of Binding Ability towards Anti-Uricase Serum," *Enzyme* 24:261-264, Karger, Switzerland (1979).

Nucci, M., et al., "The Therapeutic Value of Poly(Ethylene Glycol)-Modified Proteins," *Adv. Drug Deliv. Rev.* 6:133-151, Elsevier Science Publishers, Netherlands (1991).

Osman, A., et al., "Liver Uricase in *Camelus dromedarius*: Purification and Properties," *Comp. Biochem. Physiol.* 94B:469-474, Pergamon Press Plc., United States (1989).

Palleroni, A., et al., "Interferon Immunogenicity: Preclinical Evaluation of Interferon-α2a," *J. Interferon Cyto. Res.* 17:S23-S27, Mary Ann Liebert, Inc., United States (Jul. 1997).

Pitts, O., et al., "Uricase: Subunit Composition and Resistance to Denaturants," *Biochem.* 13:888-892, American Chemical Society, United States (1974).

Portsmann, B., et al., "Comparison of Chromogens for the Determination of Horseradish Peroxidase as a Marker in Enzyme Immunoassay," *J. Clin. Chem. Clin. Biochem.* 19:435-439, Waiter de Gruyter & Co., Germany (1981).

Pui, C., et al., "Urate oxidase in prevention and treatment of hyperuricemia associated with lymphoid malignancies," *Leukemia* 11:1813-1816, Stockon Press, United States (Nov. 1997).

Saifer, M., et al., "Improved Conjugation of Cytokines Using High Molecular Weight Poly(ethylene glycol): PEG-GM-CSF as a Prototype," *Polymer. Prepr.* 38:575-576, American Chemical Society, United States (Apr. 1997).

Saifer, M., et al., "Plasma Clearance and Immunologic Properties of Long-Acting Superoxide Dismutase Prepared Using 35,000 to 120,000 Dalton Poly-Ethylene Glycol," in *Free Radicals in Diagnostic Medicine*, Armstrong, D., ed., Plenum Press, New York, NY, pp. 377-387 (1994).

Sakane, T. and W. Pardridge, "Carboxyl-directed Pegylation of Brain-derived Neurotrophic Factor Markedly Reduces Systemic Clearance with Minimal Loss of Biologic Activity," *Pharm. Res.* 14:1085-1091, Plenum Publishing Corporation, United States (Aug. 1997).

Sartore, L., et al., "Enzyme Modification by MPEG with an Amino Acid or Peptide as Spacer Arms," *Appl. Biochem. Biotechnol.* 27:45-54, Humana Press, United States (1991).

Savoca, K., et al., "Induction of Tolerance in Mice by Uricase and Monomethyoxypolyethylene Glycol-Modified Uricase," *Int. Archs. Allergy Appl. Immun.* 75:58-67, Karger, Switzerland (1984).

Shearwater Polymers Inc., "Functionalized Biocompatible Polymers for Research and Pharmaceuticals," in *Shearwater Polymers, Inc., Catalog*, pp. 27, 47, and 48. (Jul. 1997).

Sherman, M., et al., "Conjugation of High-Molecular Weight Poly-(ethylene glycol) to Cytokines: Granulocyte-Macrophage Colony-Stimulating Factors as Model Substrates," in: *ACS Symposuim Series 680. Poly(ethylene glycol). Chemistry and Biological Applications*, pp. 155-169, Harris, J. and Zalipsky, S., eds., American Chemical Society, Washington, D.C. (Apr. 1997).

Somack, R., et al., "Preparation of Long-Acting Superoxide Dismutase Using High Molecular Weight Polyethylene Glycol (41,000-72,000 Daltons)," *Free Rad. Res. Comms.* 12-13:553-562, Harwood Academic Publishers GmBH, Germany (1991).

Suzuki, H. and D. Verma, "Soybean Nodule-Specific Uricase (Nodulin-35) is Expressed and Assembled into a Functional Tetrametric Holoenzyme in *Escherichia coli*," *Plant Physiol.* 95:384-389, American Society of Plant Physiologists, United States (1991).

Tla, S., et al., "Urate oxidase from pig liver: biochemical and immunological properties," *Prikl. Biokhim. Mikrobiol.* 14:533-542, Izdatelstvo Nauka, Russia (1978).

Treuheit, M., et al., "Inverse Relationship of Protein Concentration and Aggregation," *Pharm. Res.* 19:511-516, Plenum Publishing Corporation, United States (Apr. 2002).

Tsuji, J., et al., "Studies on Antigenicity of the Polyethylene Glycol (PEG)-Modified Uricase," *Int. J. Immunopharmacol.* 7:725-730, Elsevier Science (1985).

Venkataseshan, V., et al., "Acute Hyperuricemic Nephropathy and Rental Failure after Transplantation," *Nephron* 56:317-321, Karger AG, Switzerland (1990).

Veronese, F., "Branded and Linear Poly(Ethylene) Glycol: Influence of the Polymer Structure on Ezymological, Pharmacokinetic, and Immunological Properties of Protein Conjugates," *J. Bioact. Compat. Polym.* 12:196-207, Tectronic Publishing Co., Inc., United Stated (Jul. 1997).

Veronese, F., et al., "Surface Modification of Proteins. Activation of Monomethoxy-Polyethylene Glycols by Phenylchloroformates and Modification of Ribonuclease and Superoxide Dismutase," *Appl. Biochem. Biotechnol.* 11:141-152, The Humana Press, Inc.(1985).

Veronese, F., et al., "New Synthetic Polymers for Enzyme and Liposome Modification," in: *ACS Symposium Series 680, Poly(Ethylene Glycol) Chemistry and Biological Applications*, Harris, J. and Zalipsky, S., eds., American Chemical Society, Washington, D.C., pp. 182-192 (Apr. 1997).

Wallrath, L., et al., "Molecular Characterization of the *Drosophila melanogaster* Urate Oxidase Gene, an Ecdysone-Repressible Gene Expressed Only in the Malpighian Tubules," *Mol. Cell. Biol.* 10:5114-5127, American Society for Microbiology, United States (1990).

Wang, L. and G. Marzluf, "Purification and Characterization of Uricase, a Nitrogen-Regulated Enzyme, from *Neurospora crassa*," *Archs. Biochem. Biophys.* 201:185-193, Academic Press, Inc. (1980).

Wang, X., et al., "Rat urate oxidase: cloning and structural analysis of the gene and 5'-flanking region," *Gene* 97:223-229, Elsevier Science Publishers B.V., Netherlands (1991).

Wu, X., et al., "Hyperuricemia and urate nephropathy in urate oxidase-deficient mice," *Proc. Nat. Acad. Sci. USA* 91:742-746, National Academy of Sciences, United States (1994).

Wu, X. et al., "Two Independent Mutational Events in the Loss of the Urate Oxidase during Hominoid Evolution," *J. Mol. Evol.* 34:78-84, Springer-Verlag, Germany (1992).

Wu, X., et al., "Urate oxidase: Primary structure and evolutionary implications," *Proc. Natl. Acad. Sci. USA* 86:9412-9416, National Academy of Sciences, United States (1989).

Yasuda, Y., et al., "Biochemical and Biopharmaceutical Properties of Macromolecular Conjugates of Uricase with Dextran Polyethylene Glycol," *Chem. Pharm. Bull.* 38:2053-2056, Pharmaceutical Society of Japan, Japan (1990).

Yeldandi, A., et al., "Human Urate Oxidase Gene: Cloning and Partial Sequence Analysis Reveal a Stop Codon within the Fifth Exon," *Biochem. Biophys. Res. Commun.* 171:641-646, Academic Press, United States (1990).

SIGMA Catalog, pp. 1002, Product Nos. U 3250, 292-8, U3500, U 9375 or U 3377(1993).

European Examination Report for related European Application No. 01 923 265.1, mailed Dec. 13, 2007, European Patent Office, Munich, DE.

Esp@cenet Database, Unverified English language abstract of JP 09-154581 A, espacenet, European Patent Office (1997).

Esp@cenet Database, Unverified English language abstract of JP 03-148298 A, espacenet.com, European Patent Office (Jun. 2003).

Esp@cenet Database, Unverified English language abstract of JP 55-099189 A, espacenet.com, European Patent Office (1980).

Unverified English language partial translation of Donadio, D., et al., "Anaphylaxis-like manifestations after intravenous injection of urate oxidase in an asthmatic child with acute leukemia," *La Nouv. Presse Med.* 10:711-712, Masson, France (1981).

Chinese Second Office Action for Chinese Appplication No. 01807750.1, issued Mar. 21, 2008, Chinese Patent Office, Beijing, China.

Patent Abstract of Japan, English language abstract of JP 55-135590 A, Japanese Patent Office (1980).

Patent Abstract of Japan, English language abstract of JP 57-192435 A, Japanese Patent Office (1982).

Patent Abstracts of Japan, Unverified English language abstract for JP 62-055079 A, Japanese Patent Office (1987).

Dialog File 351, Accession No. 8448552, Unverified WPI English language abstract for DD 279486 A1 (1990).

"PEG-uricase BioTechnology General, Duke University, Mountain View licensing agreement," R&D Focus Drug News, Accession No. 1998:2984, available on Datastar File IPNR/IPNA (Aug. 1998).

NCBI Entrez Protein (PRF) Database, deposited sequence for rat urate oxidase (NP 446220), Wang, X.D., et al., National Library of Medicine, National Institutes of Health, Accession No. 20127396, accessed at http://www.ncbi.nlm.nih.gov/protein/20127395, accessed on Dec. 10, 2003.

"E.C. 1.7.3.3., urate oxidase," BRENDA Enzyme Database, accessed at www.brenda.uni-koeln.de/ (now http://www.brenda-enzymes.org/ ), 42 pages, accessed on Mar. 27, 2008, 42 pages.

Office Action mailed on Apr. 6, 2001, in U.S. Appl. No. 09/501,730, inventors Sherman et al., filed Feb. 10, 2000.

Office Action mailed on Dec. 5, 2001, in U.S. Appl. No. 09/501,730, inventors Sherman et al., filed Feb. 10, 2000.

Office Action mailed on May 22, 2002, in U.S. Appl. No. 09/501,730, inventors Sherman et al., filed Feb. 10, 2000.

Office Action mailed on Dec. 3, 2002, in U.S. Appl. No. 09/501,730, inventors Sherman et al., filed Feb. 10, 2000.

Office Action mailed on Jun. 18, 2003, in U.S. Appl. No. 09/501,730, inventors Sherman et al., filed Feb. 10, 2000.

Office Action mailed on Nov. 17, 2003, in U.S. Appl. No. 09/501,730, inventors Sherman et al., filed Feb. 10, 2000.

Office Action mailed on Jan. 13, 2004, in U.S. Appl. No. 09/501,730, inventors Sherman et al., filed Feb. 10, 2000.

Office Action mailed on Feb. 10, 2004, in U.S. Appl. No. 09/501,730, inventors Sherman et al., filed Feb. 10, 2000.

Supplemental Notice of Allowability mailed on Feb. 24, 2004; in U.S. Appl. No. 09/501,730, inventors Sherman et al., filed Feb. 10, 2000.

Office Action mailed on Apr. 9, 2007, in U.S. Appl. No. 10/928,370, inventors Sherman et al., filed Aug. 30, 2004.

Office Action mailed on Nov. 2, 2007, in U.S. Appl. No. 10/928,370, inventors Sherman et al., filed Aug. 30, 2004.

Office Action mailed on Sep. 30, 2008, in U.S. Appl. No. 10/928,370, inventors Sherman et al., filed Aug. 30, 2004.

Office Action mailed on Jun. 22, 2009, in U.S. Appl. No. 10/928,370, inventors Sherman et al., filed Aug. 30, 2004.

Office Action mailed on Dec. 9, 2009, in U.S. Appl. No. 10/928,370, inventors Sherman et al., filed Aug. 30, 2004.

Office Action mailed on Aug. 5, 2010, in U.S. Appl. No. 10/928,370, inventors Sherman et al., filed Aug. 30, 2004.

Office Action mailed on Mar. 20, 2009, in U.S. Appl. No. 11/882,750, inventors Williams et al., filed Aug. 3, 2007.

Office Action mailed on Mar. 17, 2010, in U.S. Appl. No. 11/882,750, inventors Williams et al., filed Aug. 3, 2007.

Office Action mailed on Mar. 21, 2001, in U.S. Appl. No. 09/370,084, inventors Williams et al., filed Aug. 6, 1999.

Office Action mailed on May 21, 2001, in U.S. Appl. No. 09/370,084, inventors Williams et al., filed Aug. 6, 1999.

Office Action mailed on Sep. 13, 2002, in U.S. Appl. No. 09/370,084, inventors Williams et al., filed Aug. 6, 1999.

Office Action mailed on May 29, 2002, in U.S. Appl. No. 09/370,084, inventors Williams et al., filed Aug. 6, 1999.

Office Action mailed on Jan. 13, 2003, in U.S. Appl. No. 09/370,084, inventors Williams et al., filed Aug. 6, 1999.

Office Action mailed on Jun. 10, 2003, in U.S. Appl. No. 09/839,946, inventors Williams et al., filed Apr. 19, 2001.

Office Action mailed on Sep. 11, 2003, in U.S. Appl. No. 09/839,946, inventors Williams et al., filed Apr. 19, 2001.

Office Action mailed on Mar. 5, 2004, in U.S. Appl. No. 09/839,946, inventors Williams et al., filed Apr. 19, 2001.

Office Action mailed on Aug. 2, 2004, in U.S. Appl. No. 09/839,946, inventors Williams et al., filed on Apr. 19, 2001.

Office Action mailed on Jan. 26, 2005, in U.S. Appl. No. 09/839,946, inventors Williams et al., filed Apr. 19, 2001.

Office Action mailed on Jul. 20, 2005, in U.S. Appl. No. 09/839,946, inventors Williams et al., filed Apr. 19, 2001.

Office Action mailed on Jul. 23, 2008, in U.S. Appl. No. 09/839,946, inventors Williams et al., filed Apr. 19, 2001.

Office Action mailed on Aug. 11, 2008, in U.S. Appl. No. 09/839,946, inventors Williams et al., filed Apr. 19, 2001.

Office Action mailed on Jan. 2, 2009, in U.S. Appl. No. 09/839,946, inventors Williams et al., filed Apr. 19, 2001.

Office Action mailed on Oct. 16, 2009, in U.S. Appl. No. 09/839,946, inventors Williams et al., filed Apr. 19, 2001.

Office Action mailed on Dec. 23, 2009, in U.S. Appl. No. 09/839,946, inventors Williams et al., filed Apr. 19, 2001.

Office Action mailed Jul. 11, 2006, in U.S. Appl. No. 09/839,946, inventors Williams et al., filed Apr. 19, 2001.

Advisory Action mailed Dec. 5, 2005, in U.S. Appl. No. 09/839,946, inventors Williams et al., filed Apr. 19, 2001.

BPAI Decision mailed on Jul. 18, 2007, in U.S. Appl. No. 09/839,946, inventors Williams et al., filed Apr. 19, 2001.

Notice of Hearing mailed May 15, 2007, in U.S. Appl. No. 09/839,946, inventors Williams et al., filed Apr. 19, 2001.

Office Action mailed Mar. 22, 2010, in U.S. Appl. No. 11/833,590, inventors Williams et al., filed Aug. 13, 2007.

Notice of Allowance mailed on Dec. 1, 2010, in U.S. Appl. No. 11/833,590, inventors Williams et al., filed Aug. 3, 2007.

U.S. Trademark Registration No. 2,246,623, entitled "Puricase," filed Jul. 15, 1997, 1 page.

Rosenberg, A., "Effects of Protein Aggregates: An Immunologic Perspective," *The AAPS Journal* 8:E501-E507, American Association of Pharmaceutical Scientists, United States (Aug. 2006).

Sharma, B., "Immunogenicity of therapeutic proteins. Part 3: Impact of manufacturing changes," *Biotech. Adv.* 25:325-331, Elsevier Inc., Netherlands (Jan. 2007).

* cited by examiner

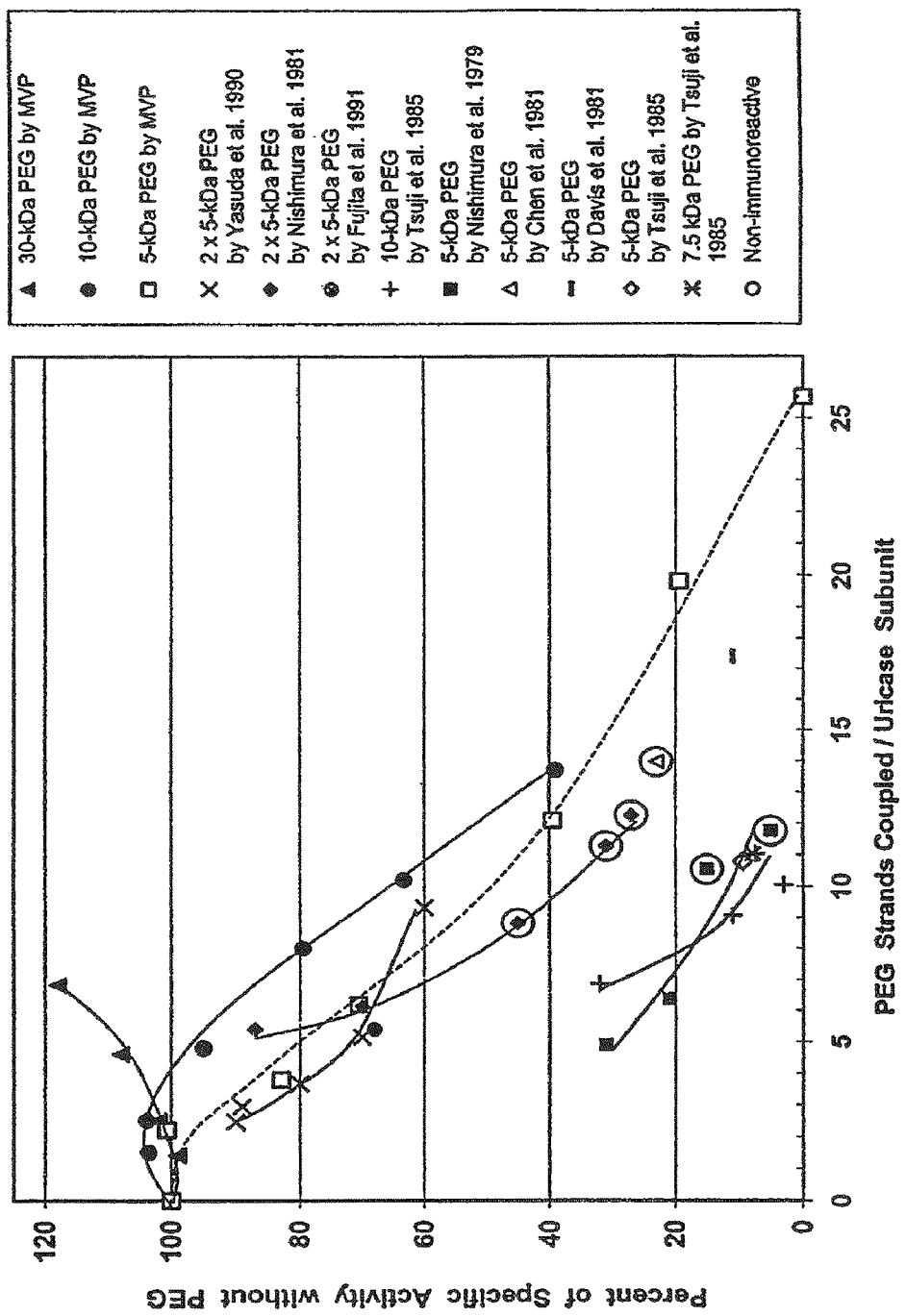
Figure 1A: Retention of Activity by PEGylated *Candida* Uricase

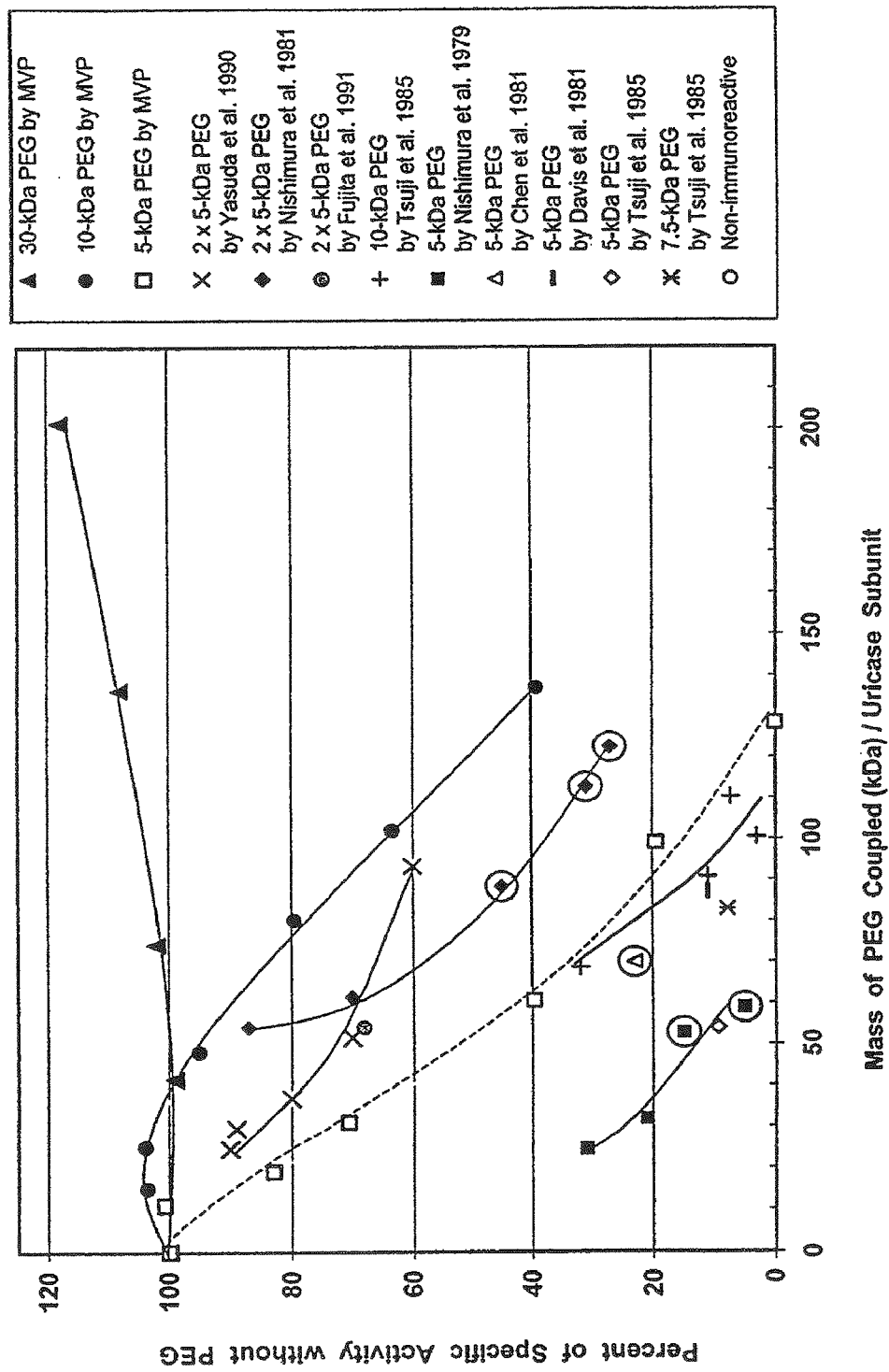
Figure 1B: Retention of Activity by PEGylated Candida Uricase

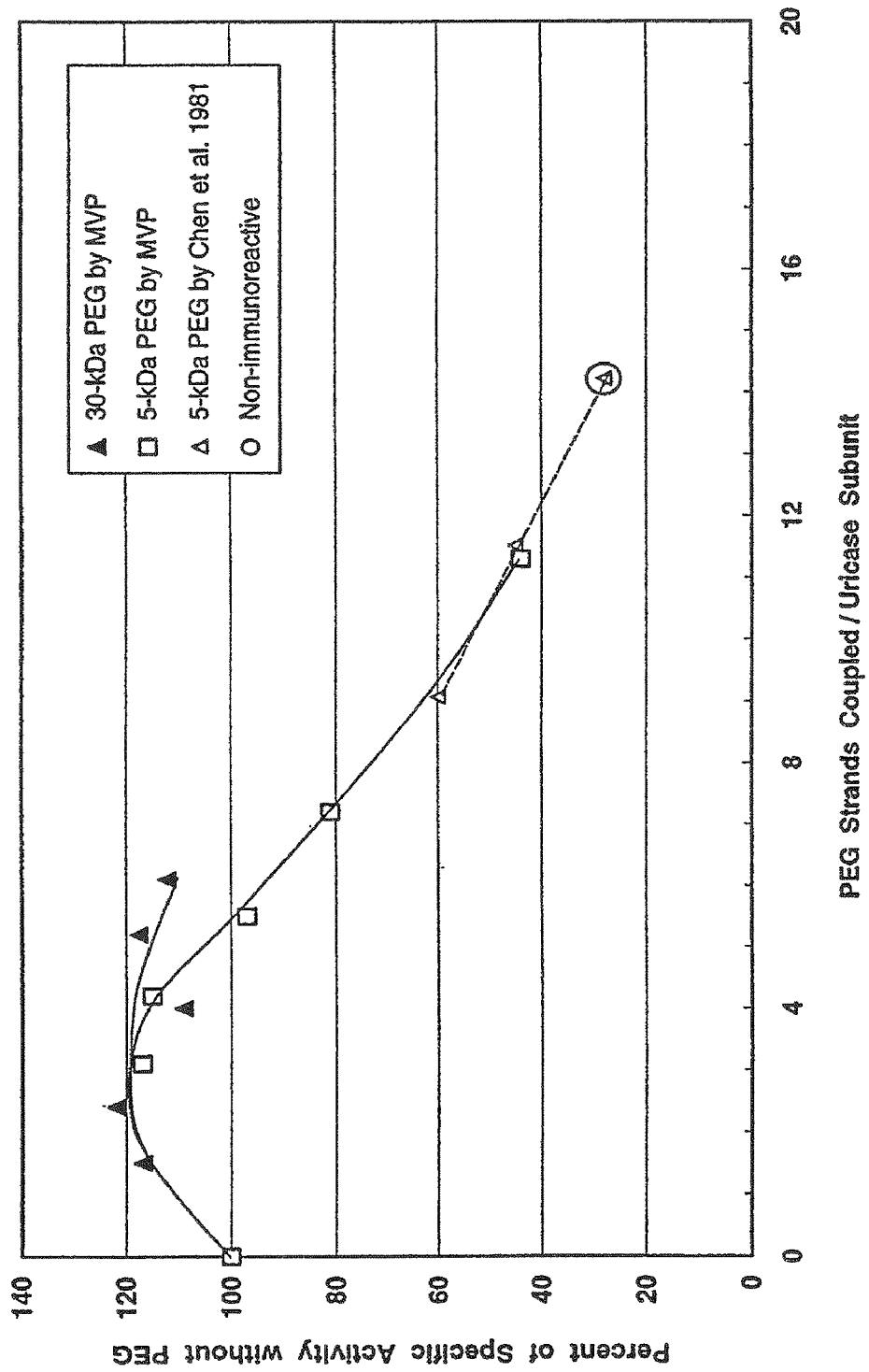
*Figure 2A:* Retention of Activity by PEGylated Porcine Uricase

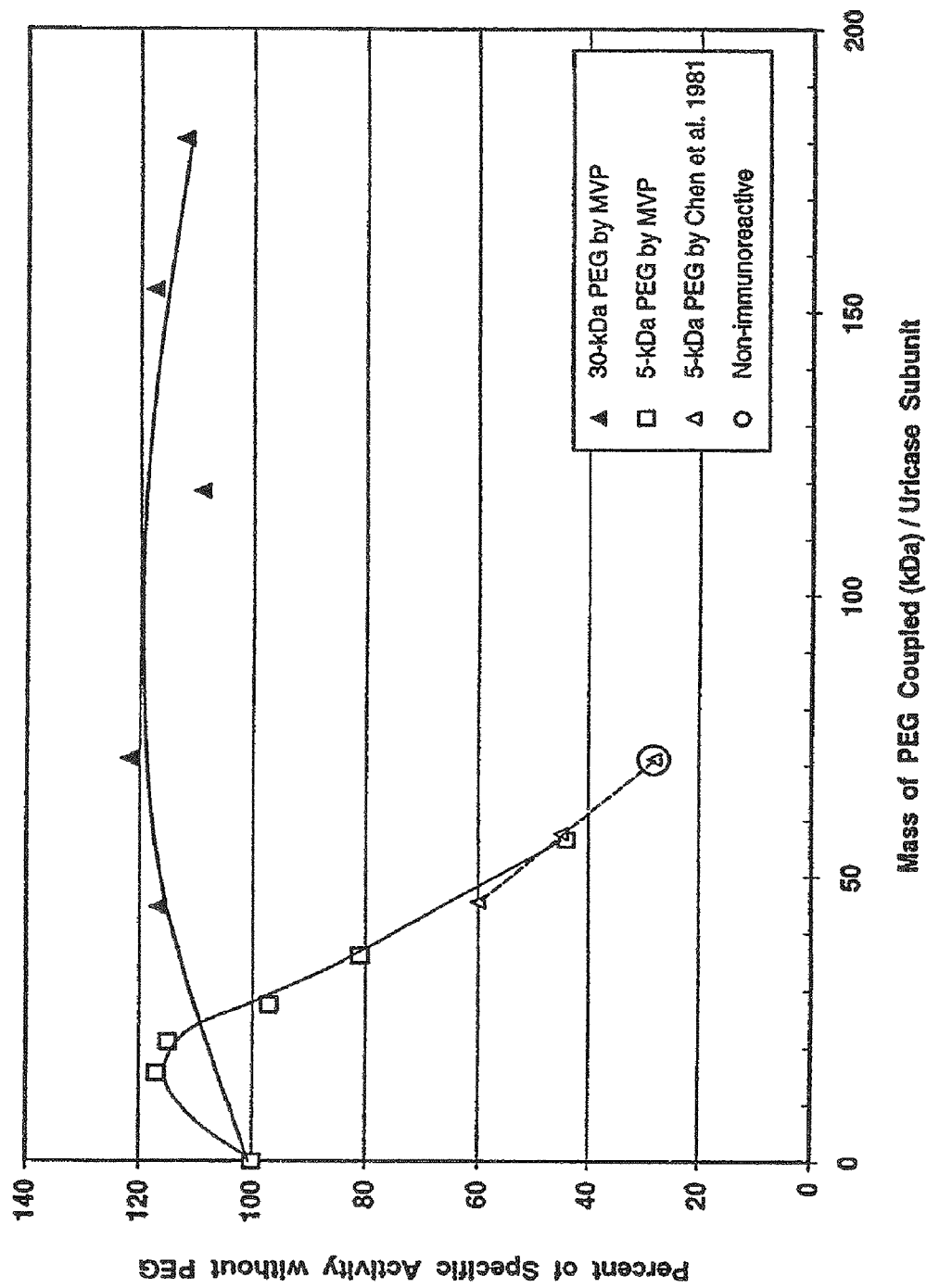
Figure 2B: Retention of Activity by PEGylated Porcine Uricase

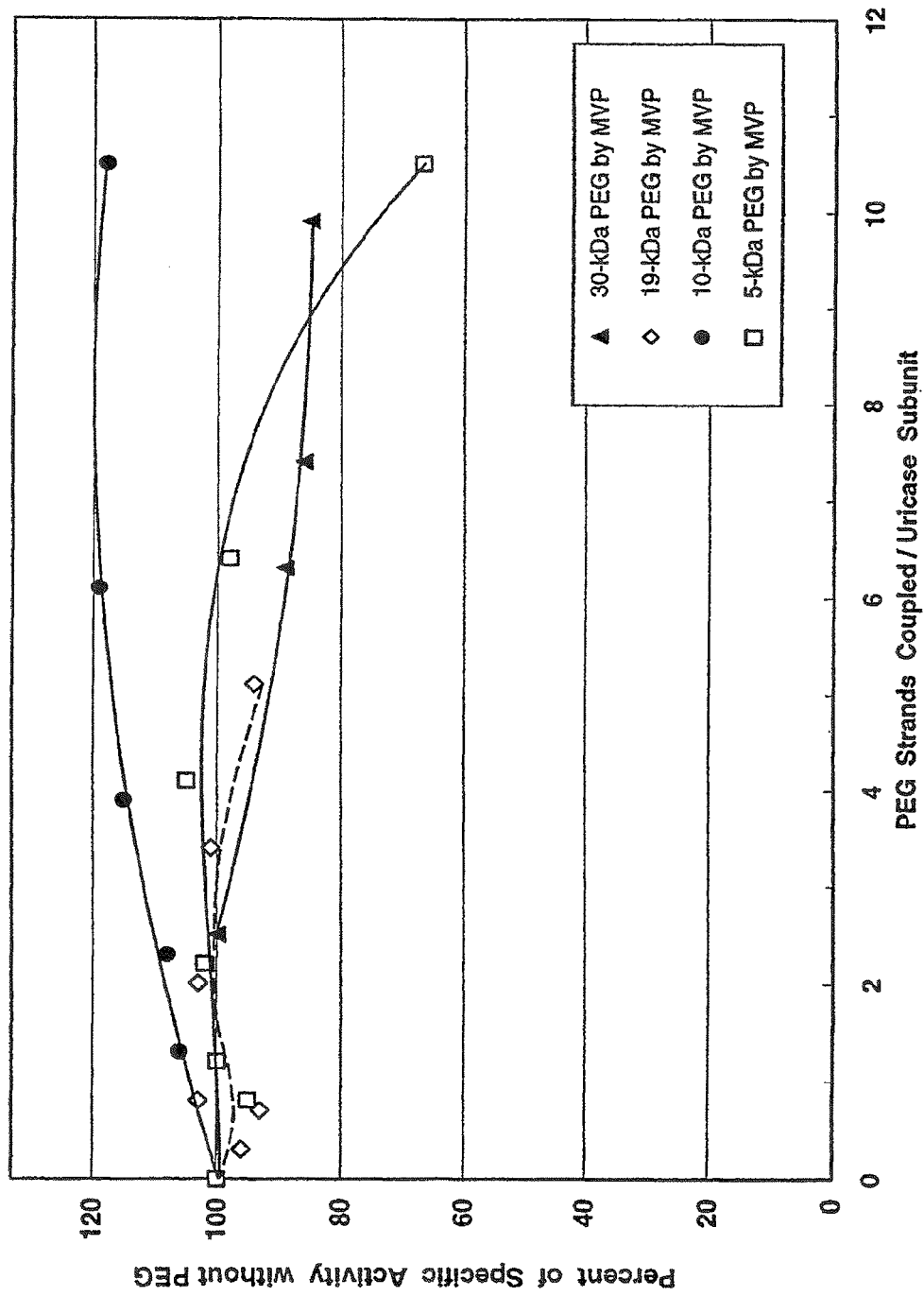
*Figure 3A:* Retention of Activity by PEGylated PBC Uricase

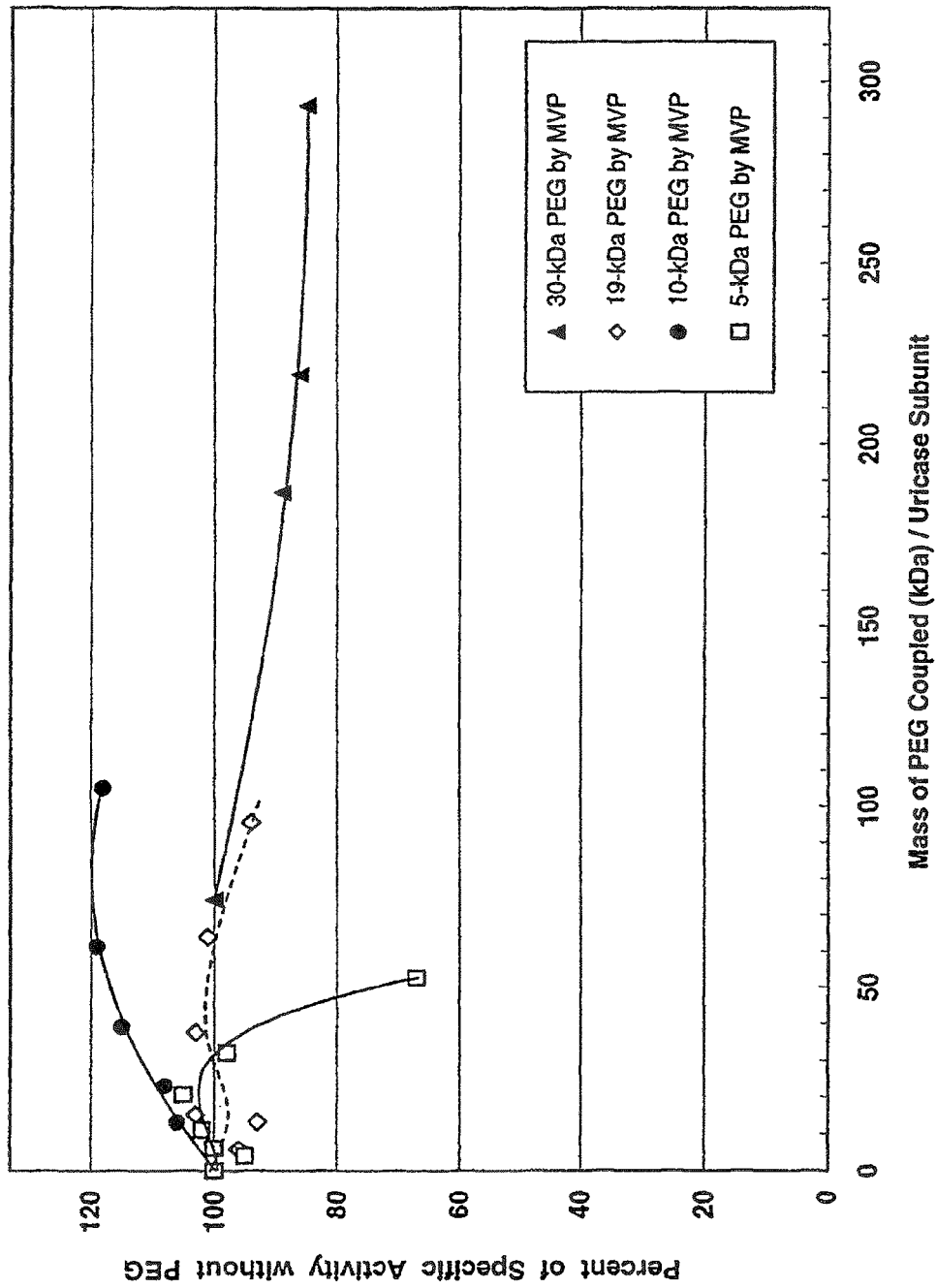
Figure 3B: Retention of Activity by PEGylated PBC Uricase

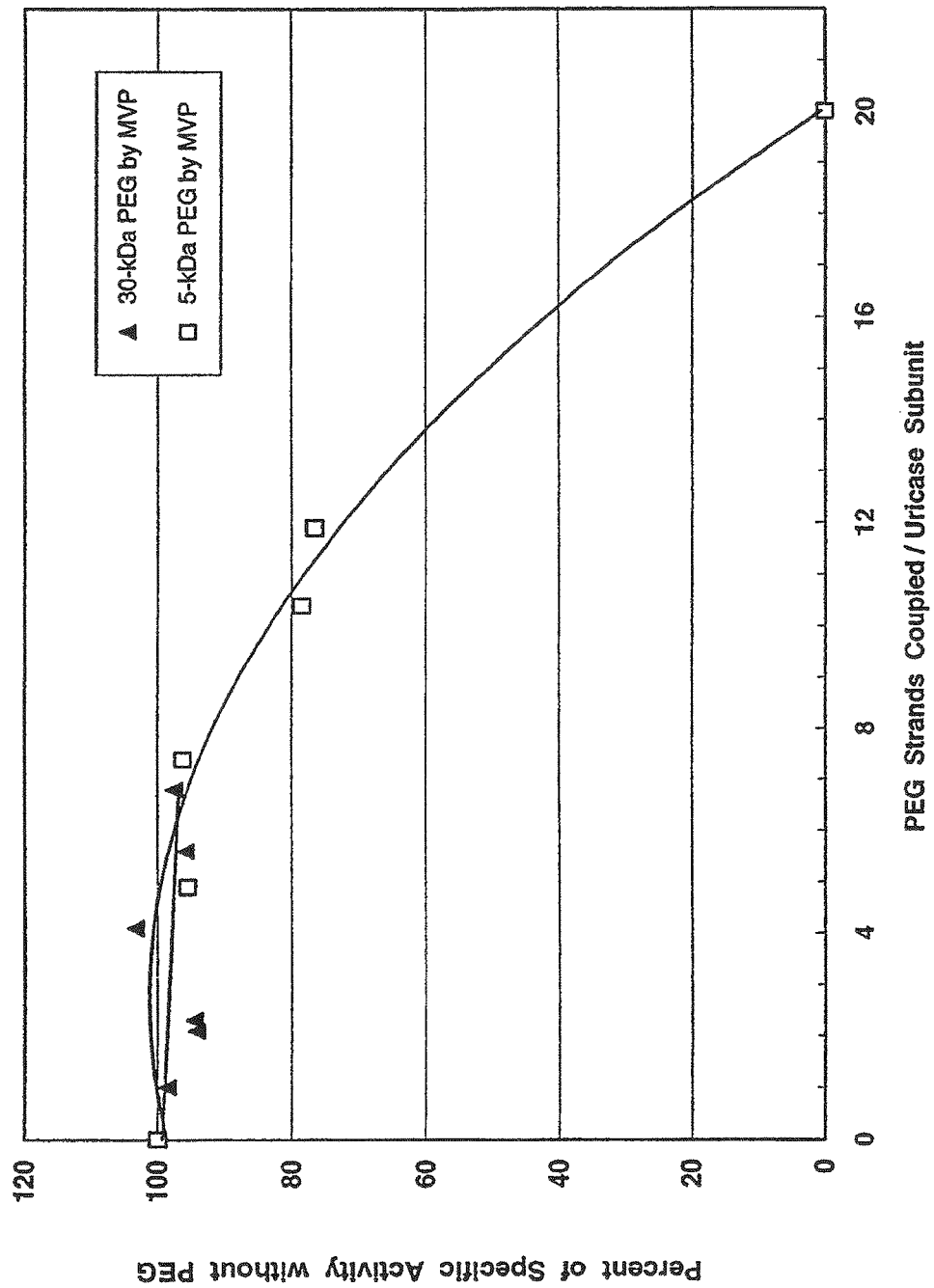
Figure 4A: Retention of Activity by PEGylated Uricozyme® (A. flavus Uricase)

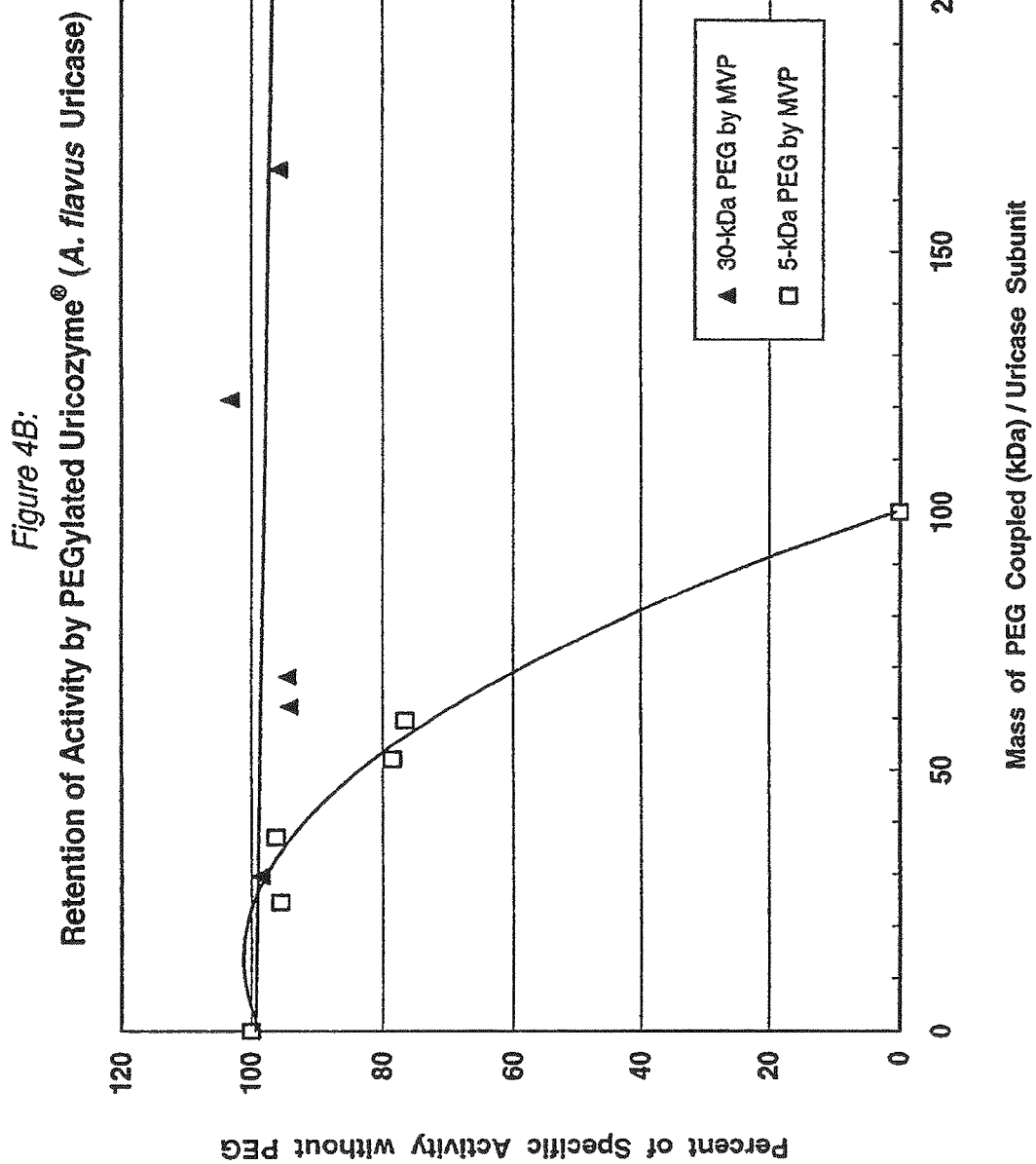
Figure 4B: Retention of Activity by PEGylated Uricozyme® (A. flavus Uricase)

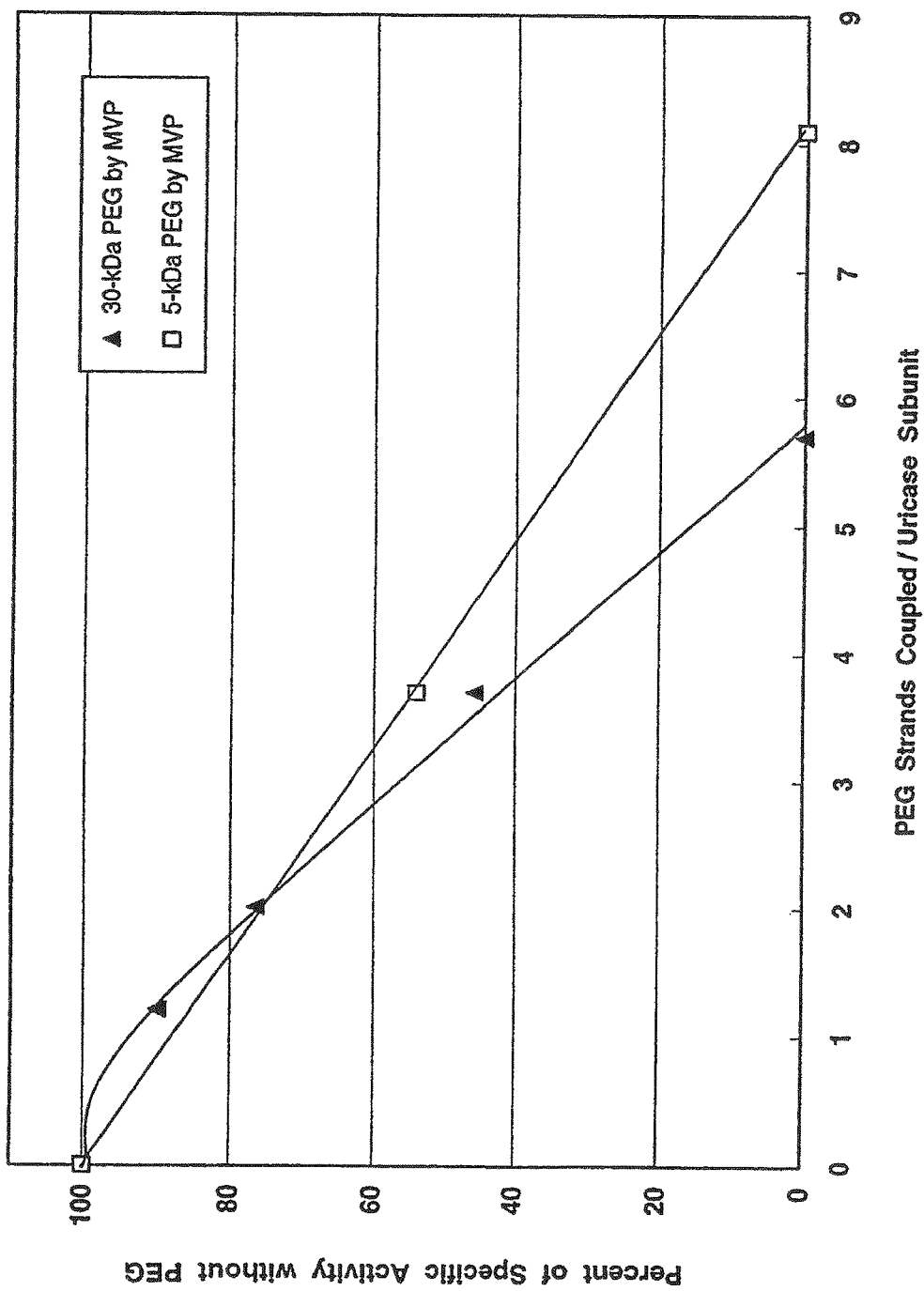
Figure 5A: Retention of Activity by PEGylated Soybean Uricase

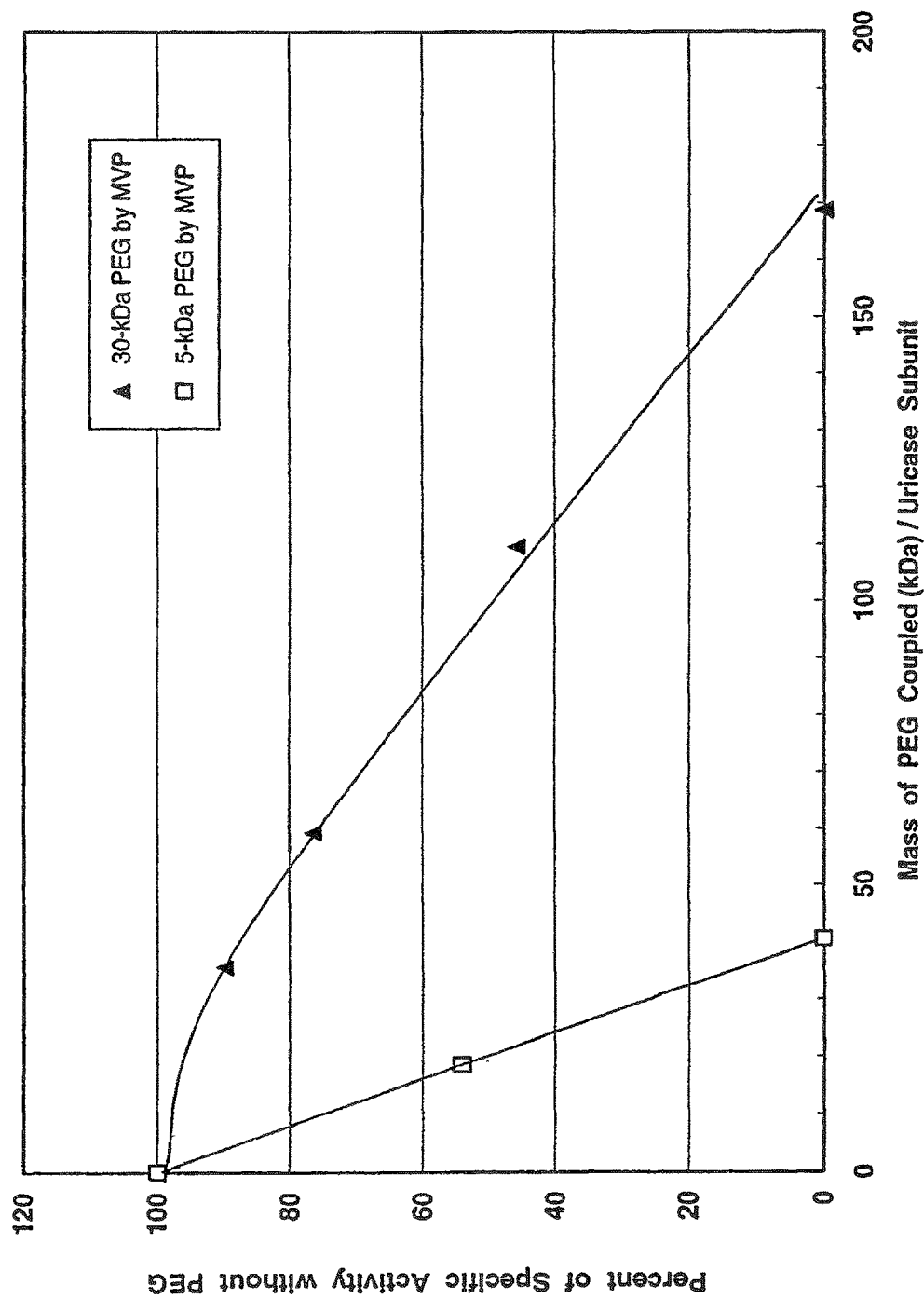
Figure 5B: Retention of Activity by PEGylated Soybean Uricase

Figure 6: Deduced amino acid sequences of Pig-Baboon Chimeric (PBC) uricase, PBC uricase that is truncated at the amino and carboxyl terminals (PBC-NT-CT) and Porcine uricase containing the mutations R291K and T301S (PKS Uricase) (SEQ ID NO:3), compared with the porcine sequence (SEQ ID NO: 1) and baboon sequence (SEQ ID NO: 2)

| | | | | | |
|---|---|---|---|---|---|
| Porcine | MAHYRNDYKK | NDEVEFVRTG | YGKDMIKVLH | IQRDGKYHSI | 40 |
| PBC | porcine sequence 1-225 → | | | | 40 |
| PBC-NT-CT | porcine sequence 1-219 → | | | | 34 |
| PKS | porcine sequence 1-288 → | | | | 40 |
| Baboon | MADYHNNYKK | NDELEFVRTG | YGKDMVKVLH | IQRDGKYHSI | 40 |
| Porcine | KEVATSVQLT | LSSKKDYLHG | DNSDVIPTDT | IKNTVNVLAK | 80 |
| PBC | porcine sequence → | | | | 80 |
| PBC-NT-CT | porcine sequence → | | | | 74 |
| PKS | porcine sequence → | | | | 80 |
| Baboon | KEVATSVQLT | LSSKKDYLHG | DNSDIIPTDT | IKNTVHVLAK | 80 |
| Porcine | FKGIKSIETF | AVTICEHFLS | SFKHVIRAQV | YVEEVPWKRF | 120 |
| PBC | porcine sequence → | | | | 120 |
| PBC-NT-CT | porcine sequence → | | | | 114 |
| PKS | porcine sequence → | | | | 120 |
| Baboon | FKGIKSIEAF | GVNICEYFLS | SFNHVIRAQV | YVEEIPWKRL | 120 |
| Porcine | EKNGVKHVHA | FIYTPTGTHF | CEVEQIRNGP | PVIHSGIKDL | 160 |
| PBC | porcine sequence → | | | | 160 |
| PBC-NT-CT | porcine sequence → | | | | 154 |
| PKS | porcine sequence → | | | | 160 |
| Baboon | EKNGVKHVHA | FIHTPTGTHF | CEVEQLRSGP | PVIHSGIKDL | 160 |
| Porcine | KVLKTTQSGF | EGFIKDQFTT | LPEVKDRCFA | TQVYCKWRYH | 200 |
| PBC | porcine sequence → | | | | 200 |
| PBC-NT-CT | porcine sequence → | | | | 194 |
| PKS | porcine sequence → | | | | 200 |
| Baboon | KVLKTTQSGF | EGFIKDQFTT | LPEVKDRCFA | TQVYCKWRYH | 200 |
| Porcine | QGRDVDFEAT | WDTVRSIVLQ | KFAGPYDKGE | YSPSVQKTLY | 240 |
| PBC | porcine sequence | → ← baboon sequence | | | 240 |
| PBC-NT-CT | porcine sequence | → ← baboon sequence | | | 234 |
| PKS | porcine sequence → | | | | 240 |
| Baboon | QCRDVDFEAT | WGTIRDLVLE | KFAGPYDKGE | YSPSVQKTLY | 240 |
| Porcine | DIQVLTLGQV | PEIEDMEISL | PNIHYLNIDM | SKMGLINKEE | 280 |
| PBC | baboon sequence → | | | | 280 |
| PBC-NT-CT | baboon sequence → | | | | 274 |
| PKS | porcine sequence → | | | | 280 |
| Baboon | DIQVLSLSRV | PEIEDMEISL | PNIHYFNIDM | SKMGLINKEE | 280 |
| Porcine | VLLPLDNPYG | RITGTVKRKL | TSRL | 304 | |
| PBC | baboon sequence → | | 304 | | |
| PBC-NT-CT | baboon sequence → | | 295 | | |
| PKS | porcine ← baboon → | | 304 | | |
| Baboon | VLLPLDNPYG | KITGTVKRKL | SSRL | 304 | |

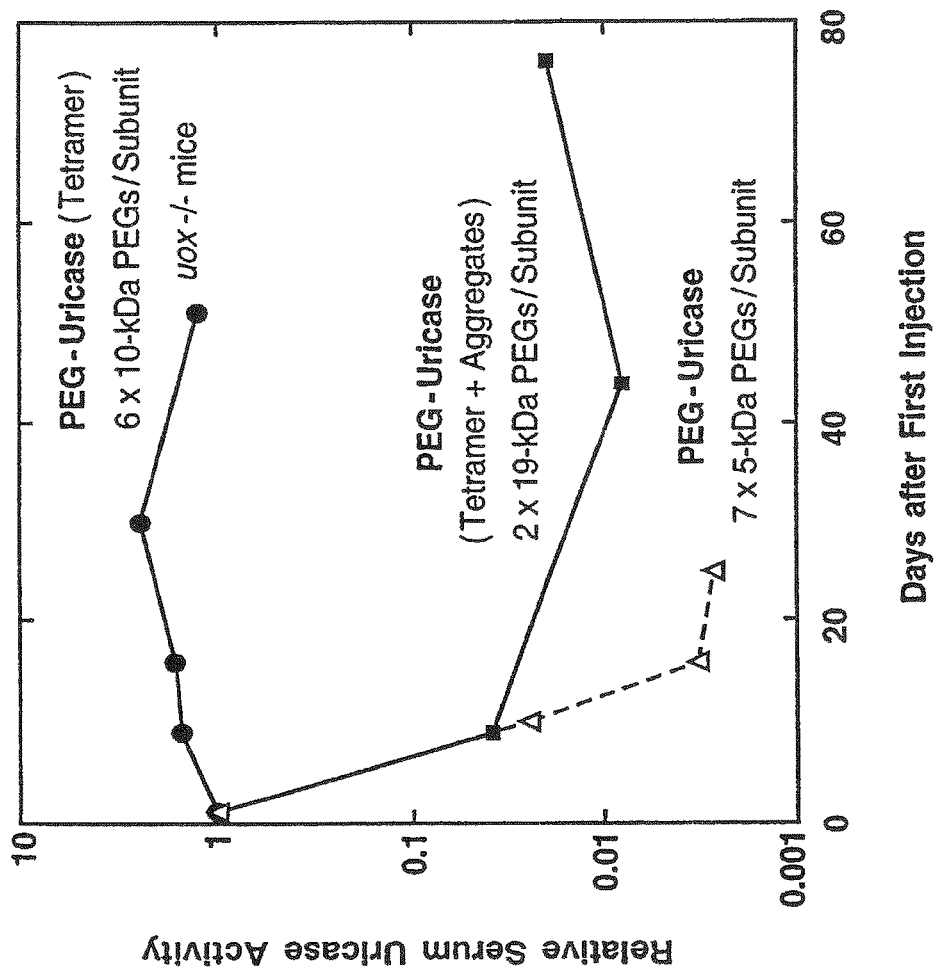
*Figure 7:* Serum Uricase Activity 24 Hours after Each PEG-Uricase Injection, Relative to the First Injection

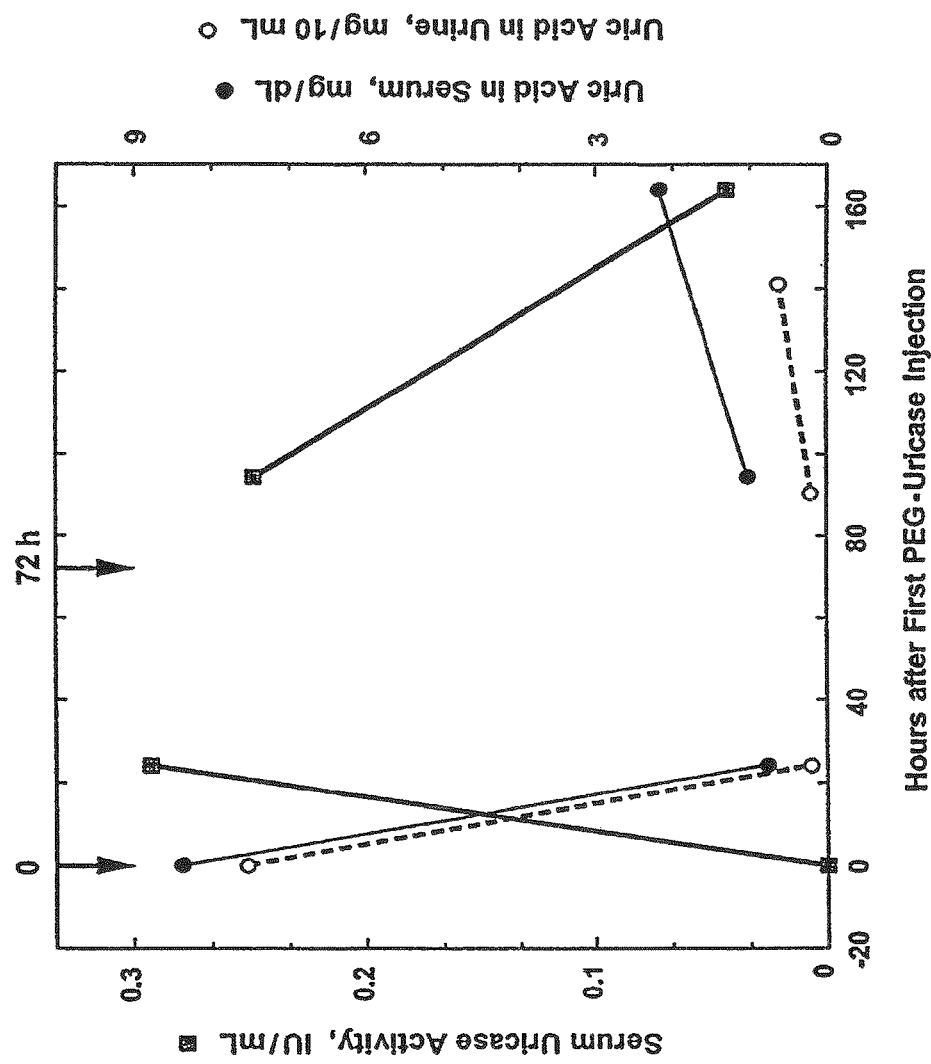
Figure 8: Inverse Relationship between Serum PEG-Uricase Activity and Uric Acid Levels in the Serum and Urine of a Uricase-Deficient Mouse

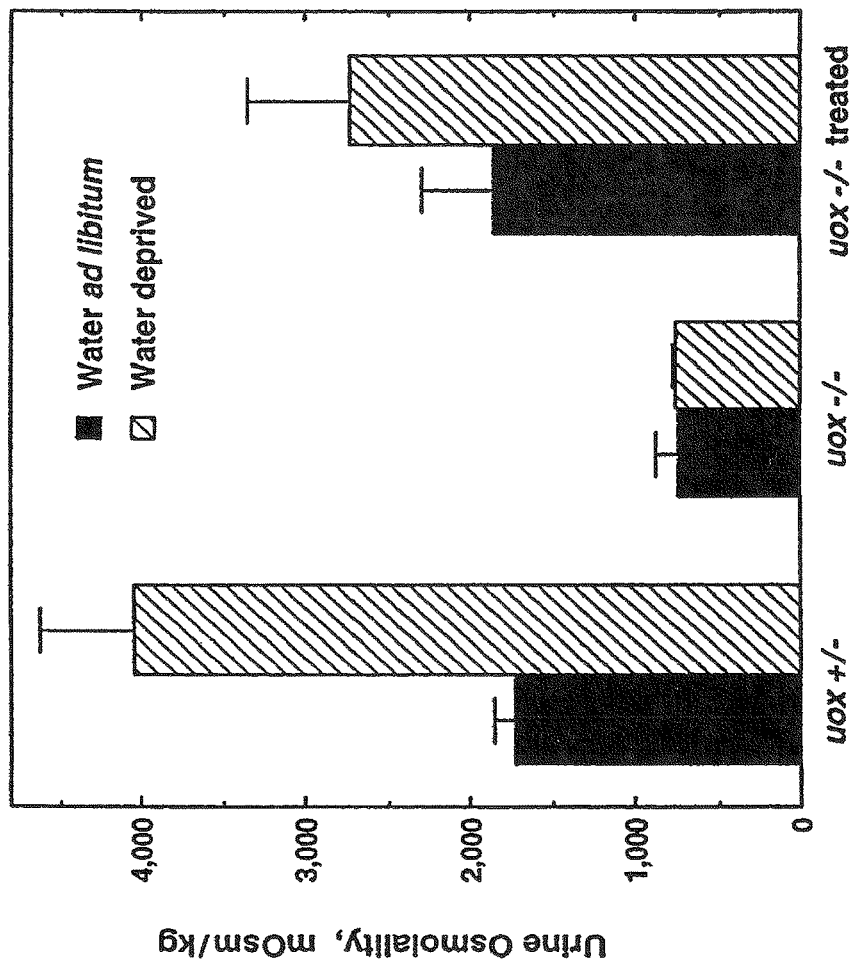
*Figure 9:* Decreased Severity of Urine-Concentrating Defect in Uricase-Deficient Mice Treated with PEG-Uricase

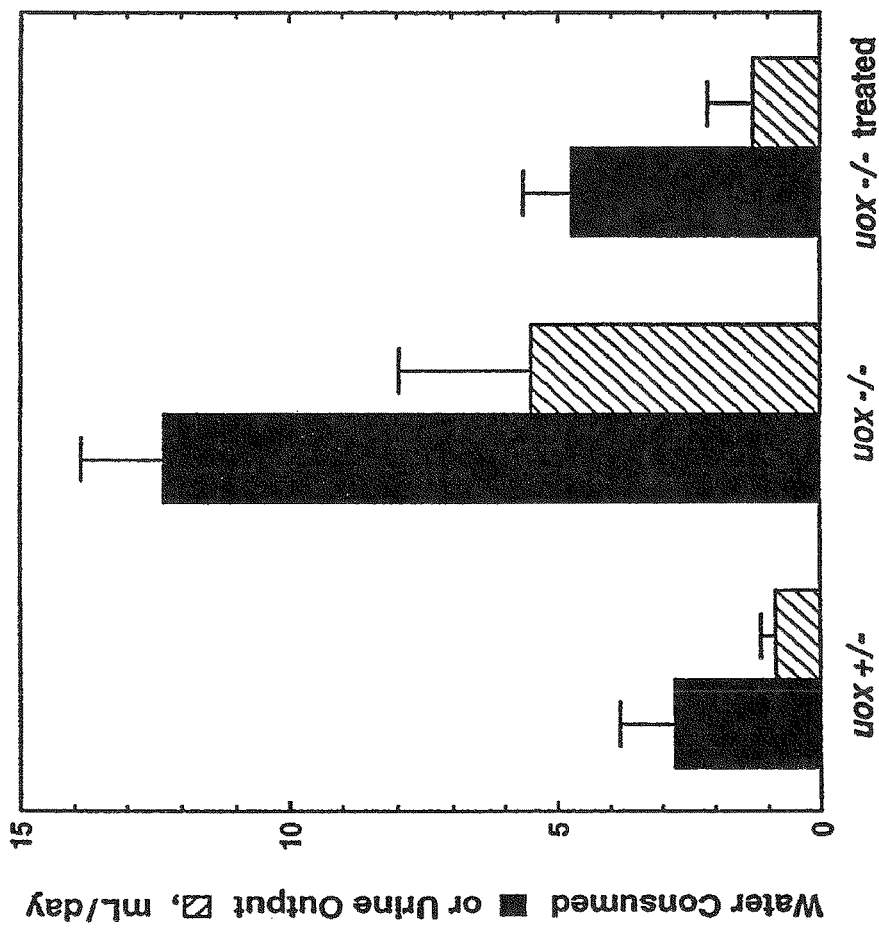
Figure 10: Decreased Severity of Nephrogenic Diabetes Insipidus in Uricase-Deficient Mice Treated with PEG-Uricase Decreased Severity of Uric Acid-Induced Nephropathy after Treatment with PEG-Uricase, as Visualized by Magnetic Resonance Microscopy

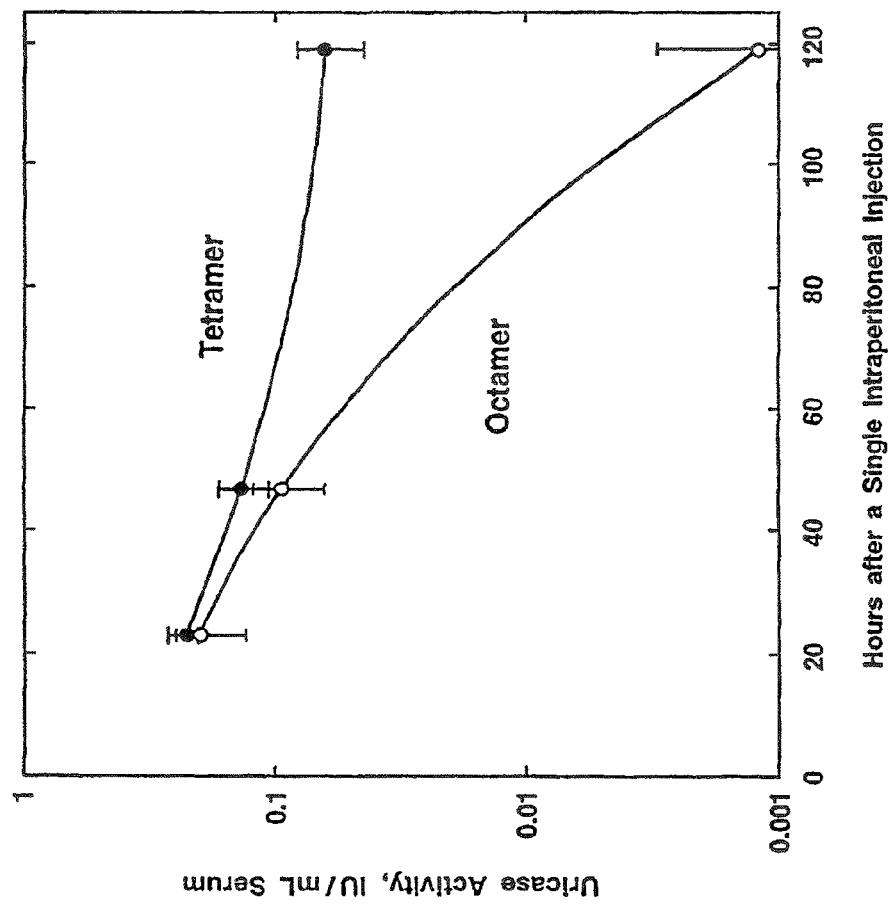
Figure 12: Clearance from the Circulation of BALB/c Mice of PBC Uricase Tetramer and Octamer Coupled to 5-6 Strands of 10-kDa PEG/Subunit

PEG-URATE OXIDASE CONJUGATES AND USE THEREOF

CROSS-REFERENCE TO RELATED APPLICATIONS

This application is a divisional of U.S. application Ser. No. 09/839,946, filed Apr. 19, 2001, now U.S. Pat. No. 7,723,089, which is a divisional of U.S. application Ser. No. 09/370,084, filed Aug. 6, 1999, now U.S. Pat. No. 6,576,235, which claims benefit under 35 U.S.C. §119(e) of U.S. Provisional Application No. 60/219,318, filed Aug. 6, 1998 now abandoned.

STATEMENT OF GOVERNMENT RIGHTS

A portion of the research described in this application was made with support from Grant DK48529 from the National Institutes of Health. Accordingly, the U.S. government may have certain rights in this invention.

FIELD OF THE INVENTION

The present invention relates to chemical modification of proteins to prolong their circulating lifetimes and reduce their immunogenicity. More specifically, the invention relates to conjugation of poly(ethylene glycols) or poly(ethylene oxides) to urate oxidases, which substantially eliminates urate oxidase immunogenicity without compromising its uricolytic activity.

BACKGROUND OF THE INVENTION

Statements contained in this background section do not constitute an admission of prior art, but instead reflect the inventors' own subjective comments on and interpretations of the state of the art at the time the invention was made. These interpretations may include personal, heretofore undisclosed, insights of the inventors, which insights were not themselves part of the prior art.

Urate oxidases (uricases; E.C. 1.7.3.3) are enzymes that catalyze the oxidation of uric acid to a more soluble product, allantoin, a purine metabolite that is more readily excreted. Humans do not produce enzymatically active uricase, as a result of several mutations in the gene for uricase acquired during the evolution of higher primates. Wu, X, et al., (1992) *J Mol Evol* 34:78-84. As a consequence, in susceptible individuals, excessive concentrations of uric acid in the blood (hyperuricemia) and in the urine (hyperuricosuria) can lead to painful arthritis (gout), disfiguring urate deposits (tophi) and renal failure. In some affected individuals, available drugs such as allopurinol (an inhibitor of uric acid synthesis) produce treatment-limiting adverse effects or do not relieve these conditions adequately. Hande, K R, et al., (1984) *Am J Med* 76:47-56; Fam, A G, (1990) *Baillière's Clin Rheumatol* 4:177-192. Injections of uricase can decrease hyperuricemia and hyperuricosuria, at least transiently. Since uricase is a foreign protein in humans, however, even the first injection of the unmodified protein from *Aspergillus flavus* has induced anaphylactic reactions in several percent of treated patients (Pui, C-H, et al., (1997) *Leukemia* 11:1813-1816), and immunologic responses limit its utility for chronic or intermittent treatment. Donadio, D, et al., (1981) *Nouv Presse Méd* 10:711-712; Leaustic, M, et al., (1983) *Rev Rhum Mal Osteoartic* 50:553-554.

The sub-optimal performance of available treatments for hyperuricemia has been recognized for several decades. Kissel, P, et al., (1968) *Nature* 217:72-74. Similarly, the possibility that certain groups of patients with severe gout might benefit from a safe and effective form of injectable uricase has been recognized for many years. Davis, F F, et al., (1978) in G B Broun, et al., (Eds.) *Enzyme Engineering, Vol. 4* (pp. 169-173) New York, Plenum Press; Nishimura, H, et al., (1979) *Enzyme* 24:261-264; Nishimura, H, et al., (1981) *Enzyme* 26:49-53; Davis, S. et al., (1981) *Lancet* 2(8241):281-283; Abuchowski, A, et al., (1981) *J Pharmacol Exp Ther* 219: 352-354; Chen, R H-L, et al., (1981) *Biochim Biophys Acta* 660:293-298; Chua, C C, et al., (1988) *Ann Int Med* 109:114-117; Greenberg, M L, et al., (1989) *Anal Biochem* 176:290-293. Uricases derived from animal organs are nearly insoluble in solvents that are compatible with safe administration by injection. U.S. Pat. No. 3,616,231. Certain uricases derived from plants or from microorganisms are more soluble in medically acceptable solvents. However, injection of the microbial enzymes quickly induces immunological responses that can lead to life-threatening allergic reactions or to inactivation and/or accelerated clearance of the uricase from the circulation. Donadio, et al., (1981); Leaustic, et al., (1983). Enzymes based on the deduced amino acid sequences of uricases from mammals, including pig and baboon, or from insects, such as, for example, *Drosophila melanogaster* or *Drosophila pseudoobscura* (Wallrath, L L, et al., (1990) *Mol Cell Biol* 10:5114-5127), have not been suitable candidates for clinical use, due to problems of immunogenicity and insolubility at physiological pH.

Covalent modification of proteins with poly(ethylene glycol) or poly(ethylene oxide) (both referred to as PEG), has been used to increase protein half-life and reduce immunogenicity. U.S. Pat. Nos. 4,179,337, 4,766,106, and 4,847,325; Saifer, M G P, et al., (1994) *Adv Exp Med Biol* 366:377-387. The coupling of PEG of high molecular weight to produce conjugates with prolonged circulating lifetimes and/or decreased immunogenicity, while conserving functional activity, was previously demonstrated for another enzyme, superoxide dismutase (Somack, R, et al., (1991) *Free Rad Res Commun* 12-13:553-562; U.S. Pat. Nos. 5,283,317 and 5,468,478) and for other types of proteins, e.g., cytokines (Saifer, M G P, et al., (1997) *Polym Preprints* 38:576-577; Sherman, M R, et al., (1997) in J M Harris, et al., (Eds.), *Poly (ethylene glycol) Chemistry and Biological Applications. ACS Symposium Series* 680 (pp. 155-169) Washington, D.C.: American Chemical Society). Conjugates of uricase with polymers other than PEG have also been described. U.S. Pat. No. 4,460, 683.

In nearly all of the reported attempts to PEGylate uricase (i.e. to covalently couple PEG to uricase), the PEG was attached primarily to amino groups, including the amino-terminal residue and the available lysine residues. In the uricases commonly used, the total number of lysines in each of the four identical subunits is between 25 (*Aspergillus flavus* (U.S. Pat. No. 5,382,518)) and 29 (pig (Wu, X, et al., (1989) *Proc Natl Acad Sci USA* 86:9412-9416)). Some of the lysines are unavailable for PEGylation in the native conformation of the enzyme. The most common approach to reducing the immunogenicity of uricase has been to couple large numbers of strands of low molecular weight PEG. This has invariably resulted in large decreases in the enzymatic activity of the resultant conjugates.

Previous investigators have used injected uricase to catalyze the conversion of uric acid to allantoin in vivo. See Pui, et al., (1997). This is the basis for the use in France and Italy of uricase from the fungus *Aspergillus flavus* (Uricozyme®) to prevent or temporarily correct the hyperuricemia associated with cytotoxic therapy for hematologic malignancies and to transiently reduce severe hyperuricemia in patients with gout. Potaux, L, et al., (1975) *Nouv Presse Méd* 4:1109-1112; Legoux, R, et al., (1992) *J Biol Chem* 267:8565-8570; U.S. Pat. Nos. 5,382,518 and 5,541,098. Because of its short circulating lifetime, Uricozyme® requires daily injections. Furthermore, it is not well suited for long-term therapy because of its immunogenicity.

A single intravenous injection of a preparation of *Candida utilis* uricase coupled to 5 kDa PEG reduced serum urate to undetectable levels in five human subjects whose average pre-injection serum urate concentration was 6.2 mg/dL, which is within the normal range. Davis, et al., (1981). The subjects were given an additional injection four weeks later, but their responses were not reported. No antibodies to uricase were detected following the second (and last) injection, using a relatively insensitive gel diffusion assay. This reference reported no results from chronic or subchronic treatments of human patients or experimental animals.

A preparation of uricase from *Arthrobacter protoformiae* coupled to 5 kDa PEG was used to temporarily control hyperuricemia in a single patient with lymphoma whose pre-injection serum urate concentration was 15 mg/dL. Chua, et al., (1988). Because of the critical condition of the patient and the short duration of treatment (four injections during 14 days), it was not possible to evaluate the long-term efficacy or safety of the conjugate.

In this application, the term "immunogenicity" refers to the induction of an immune response by an injected preparation of PEG-modified or unmodified uricase (the antigen), while "antigenicity" refers to the reaction of an antigen with preexisting antibodies. Collectively, antigenicity and immunogenicity are referred to as "immunoreactivity." In previous studies of PEG-uricase, immunoreactivity was assessed by a variety of methods, including: 1) the reaction in vitro of PEG-uricase with preformed antibodies; 2) measurements of induced antibody synthesis; and 3) accelerated clearance rates after repeated injections.

Previous attempts to eliminate the immunogenicity of uricases from several sources by coupling various numbers of strands of PEG through various linkers have met with limited success. PEG-uricases were first disclosed by F F Davis and by Y Inada and their colleagues. Davis, et al., (1978); U.S. Pat. No. 4,179,337; Nishimura, et al., (1979); Japanese Patents 55-99189 and 62-55079. The conjugate disclosed in the '337 patent was synthesized by reacting uricase of unspecified origin with a 2,000-fold molar excess of 750 dalton PEG, indicating that a large number of polymer molecules was likely to have been attached to each uricase subunit. The '337 patent discloses the coupling of either PEG or poly(propylene glycol) with molecular weights of 500 to 20,000 daltons, preferably about 500 to 5,000 daltons, to provide active, water-soluble, non-immunogenic conjugates of various polypeptide hormones and enzymes including oxidoreductases, of which uricase is one of three examples. In addition, the '337 patent emphasizes the coupling of 10 to 100 polymer strands per molecule of enzyme, and the retention of at least 40% of enzymatic activity. No test results were reported for the extent of coupling of PEG to the available amino groups of uricase, the residual specific uricolytic activity, or the immunoreactivity of the conjugate.

Data from 13 citations relating to PEGylation of uricase are summarized in Table 1. Some of these results are also presented graphically in FIGS. 1A-2B. Seven of these publications describe significant decreases in uricolytic activity measured in vitro caused by coupling various numbers of strands of PEG to uricase from *Candida utilis*. Coupling a large number of strands of 5 kDa PEG to porcine liver uricase gave similar results, as described in both the Chen publication and a symposium report by the same group. Chen, et al., (1981); Davis, et al., (1978).

Among the studies summarized in Table 1, the immunoreactivity of uricase was reported to be decreased by PEGylation in seven of them and eliminated in five of them. In three of the latter five studies, the elimination of immunoreactivity was associated with profound decreases in uricolytic activity—to at most 15%, 28%, or 45% of the initial activity. Nishimura, et al., (1979) (15% activity); Chen, et al., (1981) (28% activity); Nishimura, et al., (1981) (45% activity). In the fourth report, PEG was reported to be coupled to 61% of the available lysine residues, but the residual specific activity was not stated. Abuchowski, et al., (1981). However, a research team that included two of the same scientists and used the same methods reported elsewhere that this extent of coupling left residual activity of only 23-28%. Chen, et al., (1981). The 1981 publications of Abuchowski et al., and Chen et al., indicate that to reduce the immunogenicity of uricase substantially, PEG must be coupled to approximately 60% of the available lysine residues (Table 1). The fifth publication in which the immunoreactivity of uricase was reported to have been eliminated does not disclose the extent of PEG coupling, the residual uricolytic activity, or the nature of the PEG-protein linkage. Veronese, F M, et al., (1997) in J M Harris, et al., (Eds.), *Poly(ethylene glycol) Chemistry and Biological Applications. ACS Symposium Series* 680 (pp. 182-192) Washington, D.C.: American Chemical Society.

Conjugation of PEG to a smaller fraction of the lysine residues in uricase reduced but did not eliminate its immunoreactivity in experimental animals. Tsuji, J, et al., (1985) *Int J Immunopharmacol* 7:725-730 (28-45% of the amino groups coupled); Yasuda, Y, et al., (1990) *Chem Pharm Bull* 38:2053-2056 (38% of the amino groups coupled). The residual uricolytic activities of the corresponding adducts ranged from <33% (Tsuji, et al.) to 60% (Yasuda, et al.) of their initial values. Tsuji, et al., synthesized PEG-uricase conjugates with 7.5 kDa and 10 kDa PEGs, in addition to kDa PEG. All of the resultant conjugates were somewhat immunogenic and antigenic, while displaying markedly reduced enzymatic activities (Table 1; FIGS. 1A-1B).

A PEGylated preparation of uricase from *Candida utilis* that was safely administered twice to each of five humans was reported to have retained only 11% of its initial activity. Davis, et al., (1981). Several years later, PEG-modified uricase from *Arthrobacter protoformiae* was administered four times to one patient with advanced lymphoma and severe hyperuricemia. Chua, et al., (1988). While the residual activity of that enzyme preparation was not measured, Chua, et al., demonstrated the absence of anti-uricase antibodies in the patient's serum 26 days after the first PEG-uricase injection, using an enzyme-linked immunosorbent assay (ELISA).

As summarized in Table 1, previous studies of PEGylated uricase show that catalytic activity is markedly depressed by coupling a sufficient number of strands of PEG to decrease its immunoreactivity substantially. Furthermore, most previous preparations of PEG-uricase were synthesized using PEG activated with cyanuric chloride, a triazine derivative (2,4,6-trichloro-1,3,5-triazine) that has been shown to introduce new antigenic determinants and to induce the formation of antibodies in rabbits. Tsuji, et al., (1985).

TABLE 1

Characteristics of PEG-uricases from Previous Studies

| Source of Uricase | Coupling Linkage | Molecular Weight of PEG (kDa) | Percent of Lysines with PEG Attached | Residual Uricolytic Activity (%) | Antigenicity or Immunogenicity Comments | Reference |
|---|---|---|---|---|---|---|
| Not reported | Azide | 0.7 (diol) | Not reported | Not reported | Not reported | U.S. Pat. No. 4,179,337 |
| Candida utilis | Triazine (Cyanuric chloride) | 5 | % of "98": 20, 26, 43, 48 | 31, 21, 15, 5 | Antigenicity with rabbit serum (% of that of the unmodified enzyme) 70% 6% 0 0 | Nishimura, et al., 1979 |
| Candida utilis | PEG$_2$ triazine | 2 × 5 | 22, 25, 36, 46, 50 | 87, 70, 45, 31, 27 | 86% 49% 0 0 0 | Nishimura, et al., 1981 |
| Candida utilis | Triazine | 5 | 71 | 11 | Five men tolerated two injections in 30 days. | Davis, et al., 1981 |
| Candida utilis | Triazine according to Chen et al., 1981 | 5 | 49, 61 | Not reported Not reported | Similar immunogenicity in birds to native uricase Immunogenicity negative | Abuchowski, et al., 1981 |
| Porcine liver | Triazine | 5 | 37, 47, 58 | 60, 45, 28 | Accelerated clearance in mice " Constant Clearance (half-life ca. 8 hours) | Chen, et al., 1981 |
| Candida utilis | Triazine | 5 | 57 | 23 | Constant Clearance (half-life ca. 8 hours) | |
| Candida utilis | Triazine according to Chen, et al., 1981 | 5 | 35, 70 | Not reported Not reported | PEG decreased the immunogenicity in rabbits. PEG decreased the immunogenicity in rabbits. | Savoca, KV, et al., (1984) Int Arch Allergy Appl Immunol 75: 58-67 |
| Candida utilis | Triazine | 5 | Not reported | Not reported | PEG-uricase was given orally to chickens in liposomes (once). | Nishida, Y, et al., (1984) J Pharm Pharmacol 36: 354-355 |
| Candida utilis | Triazine | 5, 7.5, 10 | 44, 45, 28, 37, 41, 45 | 9.4, 7.8, 32, 11, 3, 7.3 | Immunogenicity was reduced, but positive in rabbits. (Antibodies are not to uricase; they cross react with PEG-superoxide dismutase.) Antigenicity tested with guinea pig antibodies was reduced. | Tsuji, et al., 1985 |
| Arthrobacter protoformiae | Not reported | 5 | Not reported | Not reported | No antibodies were detected by ELISA 26 days after the first of four PEG-uricase injections. | Chua, et al., 1988 |
| Candida utilis | PEG$_2$ triazine | 2 × 5 | 10, 12, 15, 21, 38 | 90, 89, 80, 70, 60 | Not reported Not reported Not reported Not reported Antigenicity tested with rabbit serum was reduced by 75%. | Yasuda, et al., 1990 |
| Candida utilis | PEG$_2$ triazine | 2 × 5 | 22 | 68 | Single injection. PEG increased the half-life from ca. 1 h to ca. 8 h in mice. PEG blocked clearance by liver, spleen and kidney (24-h study duration). | Fujita, et al., 1991 |
| Not reported | PEG PEG$_2$ Linkage not stated | Not reported | Not reported Reported to be the same as for PEG | Not reported Not reported | Immunogenicity in mice was decreased by 98% (PEG) or 100% (PEG$_2$). | Veronese, et al., 1997 |

Japanese Patent 3-148298 to A Sano, et al., discloses modified proteins, including uricase, derivatized with PEG having a molecular weight of 1-12 kDa that show reduced antigenicity and "improved prolonged" action, and methods of making such derivatized peptides. However, there are no disclosures regarding strand counts, enzyme assays, biological tests or the meaning of "improved prolonged." Japanese Patents 55-99189 and 62-55079, both to Y Inada, disclose uricase conjugates prepared with PEG-triazine or bis-PEG-triazine (denoted as PEG$_2$ in Table 1), respectively. See Nishimura, et al., (1979 and 1981). In the first type of conjugate, the molecular weights of the PEGs were 2 kDa and 5 kDa, while in the second, only 5 kDa PEG was used. Nishimura, et al., (1979) reported the recovery of 15% of the uricolytic activity after modification of 43% of the available lysines with linear 5 kDa PEG, while Nishimura, et al., (1981) reported the recovery of 31% or 45% of the uricolytic activity after modification of 46% or 36% of the lysines, respectively, with PEG$_2$.

SUMMARY OF THE INVENTION

Previous studies teach that when a significant reduction in the immunogenicity and/or antigenicity of uricase is achieved by PEGylation, it is invariably associated with a substantial loss of uricolytic activity. The safety, convenience and cost-effectiveness of biopharmaceuticals are all adversely impacted by decreases in their potencies and the resultant need to increase the administered dose. Thus, there is a need for a safe and effective alternative means for lowering elevated levels of uric acid in body fluids, including blood and urine. The present invention provides a substantially non-immunogenic PEG-uricase that retains all or nearly all of the uricolytic activity of the unmodified enzyme.

One embodiment of the present invention is a conjugate of urate oxidase (uricase) that retains at least about 75% of the uricolytic activity of unconjugated uricase and has substantially reduced immunogenicity. This embodiment includes a purified uricase in which each subunit may be covalently linked to an average of 2 to 10 strands of PEG, which may be linear or branched, wherein each molecule of PEG may have a molecular weight between about 5 kDa and 100 kDa. The uricase of this aspect of the invention may be recombinant. Whether recombinant or not, the uricase may be of mammalian origin. In one aspect of this embodiment, the uricase may be porcine, bovine or ovine liver uricase. In another aspect of this embodiment, the uricase may be chimeric. The chimeric uricase may contain portions of porcine liver and/or baboon liver uricase. For example, the chimeric uricase may be pig-baboon chimeric uricase (PBC uricase) or porcine uricase containing the mutations R291K and T301S (PKS uricase) (see sequences in FIG. 6 and results of physiological and immunological studies in FIGS. 7-12). Alternatively, the uricase may be baboon liver uricase in which tyrosine 97 has been replaced by histidine, whereby the specific activity of the uricase may be increased by at least about 60%. The uricase of the invention, whatever the origin, may also be in a form that is truncated, either at the amino terminal, or at the carboxyl terminal, or at both terminals. Likewise, the uricase may be fungal or microbial uricase. In one aspect of this embodiment, the fungal or microbial uricase may be a naturally occurring or recombinant form of uricase from *Aspergillus flavus, Arthrobacter globiformis* or *Candida utilis*. Alternatively, the uricase may be an invertebrate uricase, such as, for example, a naturally occurring or recombinant form of uricase from *Drosophila melanogaster* or *Drosophila pseudoobscura*. The uricase of the invention may also be a plant uricase, for example, a naturally occurring or recombinant form of uricase from soybean root nodule (*Glycine max*). The PEG may have an average molecular weight between about 5 kDa and 100 kDa; preferably the PEG may have an average molecular weight between about 10 kDa and 60 kDa; more preferably, the PEG may have an average molecular weight between about 20 kDa and about 40 kDa, such as, for example, 30 kDa. The average number of covalently coupled strands of PEG may be 2 to 10 strands per uricase subunit; preferably, the average number of covalently coupled strands may be 3 to 8 per subunit; more preferably, the average number of strands of PEG may be 4 to 6 per subunit. In one aspect of this embodiment, the uricase may be tetrameric. The strands of PEG may be covalently linked to uricase via urethane (carbamate) linkages, secondary amine linkages, and/or amide linkages. When the uricase is a recombinant form of any of the uricases mentioned herein, the recombinant form may have substantially the sequence of the naturally occurring form.

Another embodiment of the present invention is a pharmaceutical composition for lowering uric acid levels in body fluids, containing any of the PEG-uricase conjugates described above and a pharmaceutically acceptable carrier. The composition may be stabilized by lyophilization and also may dissolve promptly upon reconstitution to provide solutions suitable for parenteral administration.

The present invention also provides a method for lowering uric acid levels in body fluids and tissues of a mammal. The method includes administering to a mammal an effective uric acid-lowering amount of PEG-uricase. The PEG-uricase may be a purified uricase of two or more subunits in which each subunit may be covalently linked to an average of 2 to 10 strands of linear or branched PEG, wherein each molecule of PEG may have a molecular weight between about 5 kDa and 100 kDa, in a pharmaceutically acceptable carrier. The mammal may be a human. The administering step may be, for example, injection by intravenous, intradermal, subcutaneous, intramuscular or intraperitoneal routes or inhalation of an aerosolized preparation. The elevated uric acid levels may be in blood, urine and/or other body fluids and tissues, and may be associated with gout, tophi, renal insufficiency, organ transplantation or malignant disease.

Other embodiments of the present invention are a method for isolating a tetrameric form of uricase from a solution containing multiple form is of uricase and the product of that method. Initially, the solution may contain tetrameric uricase and uricase aggregates. The method may include the steps of: applying the solution to at least one separation column at a pH between about 9 and 10.5, such as, for example, 10.2; recovering fractions of the eluate and identifying those that may contain isolated tetrameric uricase, wherein the fractions are substantially free of uricase aggregates; and pooling the fractions of the isolated tetrameric uricase. The separation column may be based on ion exchange, size exclusion, or any other effective separation property. The method may also include analysis of the fractions to determine the presence of tetrameric uricase and/or the absence of uricase aggregates. For example, such analysis may include high performance liquid chromatography (HPLC), other chromatographic methods, light scattering, centrifugation and/or electrophoresis. In one aspect of this embodiment, the purified tetrameric uricase may contain less than about 10% uricase aggregates.

BRIEF DESCRIPTION OF THE DRAWINGS

FIG. 1A shows the retention of activity by PEGylated uricase from *Candida* wills as a function of the number of strands of PEG coupled per subunit.

FIG. 1B shows the retention of activity by PEGylated uricase from *Candida utilis* as a function of the total mass of PEG coupled per subunit.

FIG. 2A shows the retention of activity by PEGylated uricase from porcine liver as a function of the number of strands of PEG coupled per subunit.

FIG. 2B shows the retention of activity by PEGylated uricase from porcine liver as a function of the total mass of PEG coupled per subunit.

FIG. 3A shows the retention of activity by PEGylated pig-baboon chimeric (PBC) uricase as a function of the number of strands coupled per subunit.

FIG. 3B shows the retention of activity by PEGylated PBC uricase as a function of the total mass of PEG coupled per subunit.

FIG. 4A shows the retention of activity by PEGylated uricase from *Aspergillus* flavus as a function of the number of strands of PEG coupled per subunit.

FIG. 4B shows the retention of activity by PEGylated uricase from *Aspergillus* flavus as a function of the total mass of PEG coupled per subunit.

FIG. 5A shows the retention of activity by PEGylated recombinant soybean root nodule uricase as a function of the number of strands of PEG coupled per subunit.

FIG. 5B shows the retention of activity by PEGylated recombinant soybean root nodule uricase as a function of the total mass of PEG coupled per subunit.

FIG. 6 shows the deduced amino acid sequences of pig-baboon chimeric uricase (PBC uricase), PBC uricase that is truncated at both the amino and carboxyl terminals (PBC-NT-CT) and porcine uricase containing the mutations R291K and T301S (PKS uricase), compared with the porcine and baboon sequences.

FIG. 7 shows the activity of uricase in mouse serum 24 h after each of four or five intraperitoneal injections of PEG-modified PBC uricase, relative to the value 24 h after the first injection.

FIG. 8 shows the inverse relationship between the activity of injected PEG-modified PBC uricase in the serum of a uricase-deficient mouse and the concentrations of uric acid in the serum and urine.

FIG. 9 shows the decreased severity of a urine-concentrating defect in uricase-deficient (uox −/−) mice that were treated with PEG-modified PBC uricase.

FIG. 10 shows the decreased severity of nephrogenic diabetes insipidus in uricase-deficient (uox −/−) mice that were treated with PEG-modified PBC uricase.

FIG. 12 shows the accelerated clearance from the circulation of BALB/c mice of injected PBC uricase octamer, compared with the tetramer, when both were coupled to 5-6 strands of 10 kDa PEG per subunit.

DETAILED DESCRIPTION OF THE PREFERRED EMBODIMENTS

Figure 11:
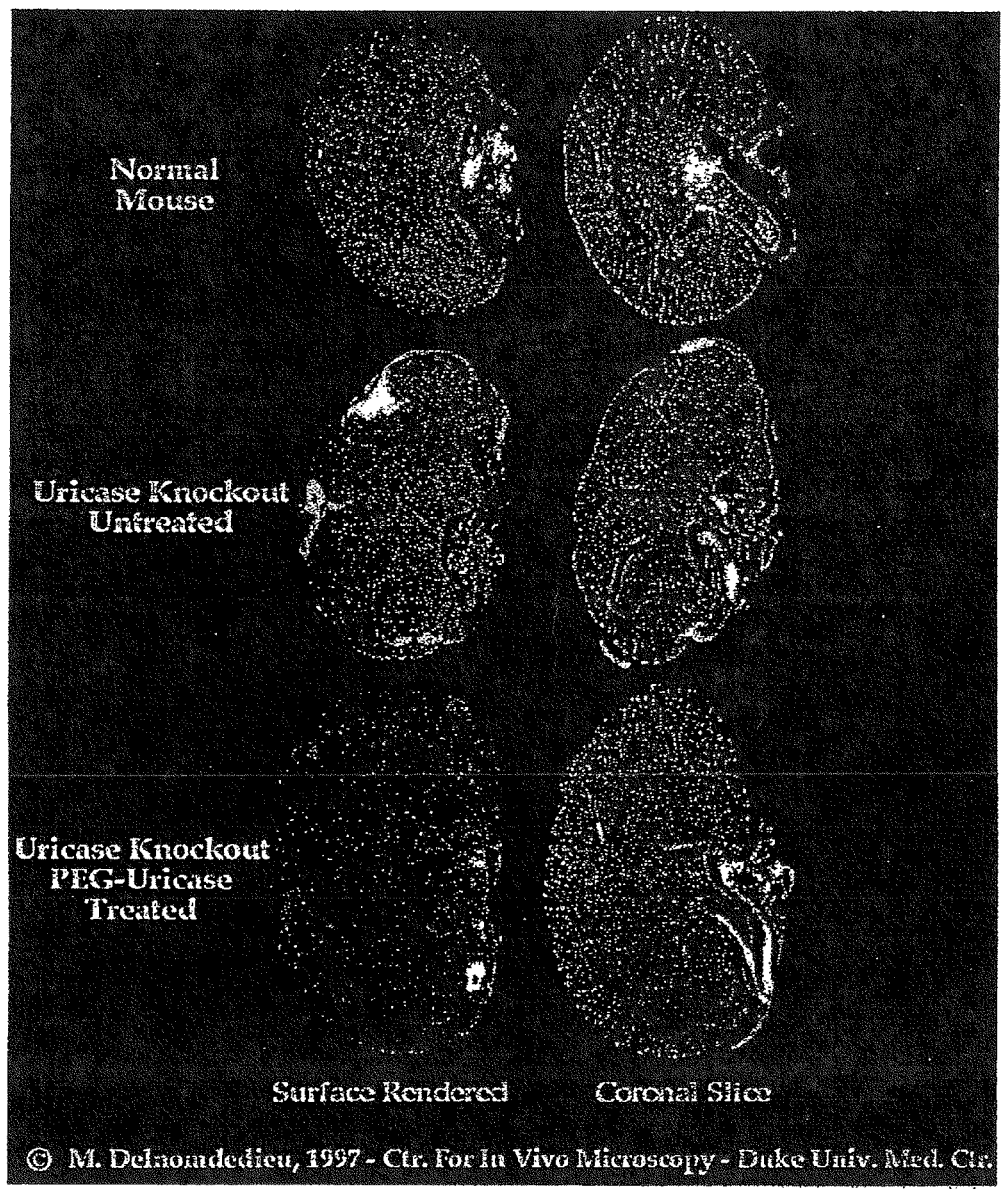
FIG. 11 shows the decreased severity of uric acid-induced nephropathy, as visualized by magnetic resonance microscopy, in uricase-deficient (uox −/−) mice that were treated with PEG-modified PBC uricase.

The present invention provides improved conjugates of water-soluble polymers, preferably poly(ethylene glycols) or poly(ethylene oxides), with uricases. The invention also provides pharmaceutical compositions of the improved conjugates. These conjugates are substantially non-immunogenic and retain at least 75%, preferably 85%, and more preferably 95% or more of the uricolytic activity of the unmodified enzyme. Uricases suitable for conjugation to water-soluble polymers include naturally occurring urate oxidases isolated from bacteria, fungi and the tissues of plants and animals, both vertebrates and invertebrates, as well as recombinant forms of uricase, including mutated, hybrid, and/or truncated enzymatically active variants of uricase. Water-soluble polymers suitable for use in the present invention include linear and branched poly(ethylene glycols) or poly(ethylene oxides), all commonly known as PEGs. Examples of branched PEG are the subject of U.S. Pat. No. 5,643,575. One preferred example of linear PEG is monomethoxy PEG, of the general structure $CH_3O-(CH_2CH_2O)_nH$, where n varies from about 100 to about 2,300.

One preferred mammalian uricase is recombinant pig-baboon chimeric uricase, composed of portions of the sequences of pig liver and baboon liver uricase, both of which were first determined by Wu, et al., (1989). One example of such a chimeric uricase contains the first 225 amino acids from the porcine uricase sequence (SEQ ID NO: 1) and the last 79 amino acids from the baboon uricase sequence (SEQ ID NO: 2) (pig-baboon uricase, or PBC uricase; see FIG. 6). Another example of such a chimeric uricase contains residues 7-225 of the porcine sequence (SEQ ID NO. 1) and residues 226-301 of the baboon sequence (SEQ ID NO. 2); this is equivalent to PBC uricase that is truncated at both the amino and carboxyl terminals (PBC-NT-CT; see FIG. 6). Another example of such a chimeric uricase contains the first 288 amino acids from the porcine sequence (SEQ ID NO: 1) and the last 16 amino acids from the baboon sequence (SEQ ID NO: 2). Since the latter sequence differs from the porcine sequence at only two positions, having a lysine (K) in place of arginine at residue 291 and a serine (S) in place of threonine at residue 301, this mutant is referred to as pig-K-S or PKS uricase. PKS, PBC and PBC-NT-CT uricases each have one more lysine residue and, hence, one more potential site of PEGylation than either the porcine or baboon sequence.

The cDNAs for various mammalian uricases, including PBC uricase, PKS uricase and a recombinant baboon-like uricase, were subcloned and the optimal conditions were determined for expression in *E. coli*, using standard methods. See Erlich, H A, (Ed.) (1989) *PCR Technology. Principles and Applications for DNA Amplification*. New York: Stockton Press; Sambrook, J, et al., (1989) *Molecular Cloning. A Laboratory Manual, Second Edition*. Cold Spring Harbor, N.Y.: Cold Spring Harbor Laboratory Press. The recombinant uricases were extracted, purified and their stability and activity were assessed using a modification of standard assays. See Fridovich, I, (1965) *J Biol Chem* 240:2491-2494; Nishimura, et al., (1979), and Example 1.

In one embodiment of the invention, uricase may be conjugated via a biologically stable, nontoxic, covalent linkage to a relatively small number of strands of PEG. Such linkages may include urethane (carbamate) linkages, secondary amine linkages, and amide linkages. Various activated PEGs suitable for such conjugation are available commercially from Shearwater Polymers, Huntsville, Ala.

For example, urethane linkages to uricase may be formed by incubating uricase in the presence of the succinimidyl carbonate (SC) or 4-nitrophenyl carbonate (NPC) derivative of PEG. SC-PEG may be synthesized using the procedure described in U.S. Pat. No. 5,612,460, which is hereby incorporated by reference. NPC-PEG may be synthesized by reacting PEG with 4-nitrophenyl chloroformate according to methods described in Veronese, F M, et al., (1985) *Appl Biochem Biotechnol* 11:141-152, and in U.S. Pat. No. 5,286,637, which is hereby incorporated by reference. The methods described in the '637 patent are adapted to PEGs of higher molecular weight by adjusting the concentrations of the reactants to maintain similar stoichiometry. An alternative method of synthesis of NPC-PEG is described by Büttner, W, et al., East German Patent Specification DD 279 486 A1.

Amide linkages to uricase may be obtained using an N-hydroxysuccinimide ester of a carboxylic acid derivative of PEG (Shearwater Polymers). Secondary amine linkages may be formed using 2,2,2-trifluoroethanesulfonyl PEG (tresyl PEG; Shearwater Polymers) or by reductive alkylation using PEG aldehyde (Shearwater Polymers) and sodium cyanoborohydride.

In conjugates containing PEGs with molecular weights between 5 kDa and 30 kDa, the maximum number of strands of PEG that were coupled per subunit, while retaining at least 75% of the uricolytic activity of the unmodified enzyme, ranged from an average of 2 strands for soybean uricase to more than 10 strands for PBC uricase (see assay conditions in Example 1 and results in FIGS. 1A-5B). The latter extent of PEGylation corresponds to approximately one third of the total amino groups. In one embodiment of the invention, the average number of strands of PEG coupled per uricase subunit is between 2 and 10. In a preferred embodiment, the average number of strands of PEG coupled per uricase subunit is between 3 and 8. In a more preferred embodiment, the average number of covalently linked strands of PEG per uricase subunit is between 4 and 6. In another embodiment, the molecular weight of PEG used for the coupling reaction is between 5 kDa and 100 kDa, preferably between 10 kDa and 60 kDa, and more preferably between 20 kDa and 40 kDa, such as, for example 30 kDa.

There are several factors that may affect the choice of the optimal molecular weight and number of strands of PEG for coupling to a given form of uricase. In general, the reduction or elimination of immunogenicity without substantial loss of uricolytic activity may require the coupling of relatively more strands of PEG of lower molecular weight, compared to relatively fewer strands of PEG of higher molecular weight. For example, either 6 strands of 20 kDa PEG per subunit or 4 strands of 30 kDa PEG per subunit might be optimally effective. Likewise, each different form of uricase may have a different optimum with respect to both the size and number of strands. See FIGS. 1A-5B.

PEG conjugation rendered all of the tested uricases soluble and stable in buffers at physiological pH, without the addition of a substrate analog or inhibitor, such as 8-azaxanthine that is used as a stabilizer in the fungal uricase (Uricozyme®) sold by Sanofi Winthrop in France and Italy. Two different conjugates of PBC uricase, one containing approximately 6 strands of 10 kDa PEG per subunit and the other containing approximately 2 strands of 19 kDa PEG per subunit, retained significant activity after incubation in mouse serum for more than one month at 37° C. In addition, several of the conjugates of this invention had circulating half-lives in mice that were greater than two days, in contrast to the approximately 8-hour or 24-hour half-lives previously reported for PEG-modified mammalian and microbial uricases. Chen, et al., (1981); Fuertges, F, et al., (1990) *J Contr Release* 11: 139-148; Fujita, T, et al., (1991) *J Pharmacobiodyn* 14:623-629. Longer half-lives of injected protein drugs make them more cost-effective and can lead to improved patient compliance. Prolonged half-life is also indicative of products that are better tolerated by the body.

When PEG conjugates of PBC uricase were prepared from the purified tetrameric form of the enzyme (four 35 kDa subunits), they displayed profoundly reduced immunogenicity in mice (FIG. 7), in contrast to the moderate immunogenicity of PEG conjugates of larger forms of the enzyme (e.g. octamers of the 35 kDa subunit; see FIG. 12), and the very high immunogenicity of the unmodified enzyme. Repeated injections of uricase-deficient mice with PEG-uricase of the present invention eliminated their hyperuricemia for more than 2 months and protected the structure and function of their kidneys against uric acid-related damage (FIGS. 8-11).

Injections of fully active conjugates of PBC uricase with 10 kDa PEG (FIGS. 3A-3B) reduced dramatically the hyperuricemia of homozygous, uricase-deficient mice (FIG. 8). Uric acid levels in the urine were also reduced dramatically in all uricase-deficient mice treated with PEG-modified PBC uricase. Uricase-deficient mice received a series of injections with a preparation of PEG-uricase similar to that used to obtain the data in FIG. 8. This treatment reduced the severity of a urine-concentrating defect, as demonstrated by measurements of urine osmolality under normal conditions and after a 12-hour period of water deprivation (FIG. 9) and by their water consumption and urine output (FIG. 10), compared to the corresponding measurements in untreated, genetically similar mice. It was also demonstrated that ten weeks of treatment, starting within the first ten days of life, of homozygous uricase-deficient (uox −/−) "knockout" mice with a PEG-uricase of this invention decreased the severity of urate-induced disruption of the renal architecture, as visualized by magnetic resonance microscopy (FIG. 11). For microscopy methods, see Hedlund, L W, et al., (1991) *Fund Appl Toxicol* 16:787-797; Johnson, G A, et al., (1992) in J C Gore, (Ed.), *Reviews of Magnetic Resonance in Medicine, Vol.* 4 (pp. 187-219) New York: Pergamon Press.

Purified preparations of naturally occurring and recombinant uricases usually contain a mixture of aggregates of the enzyme, in addition to the tetrameric (140 kDa) form. The percentage of each uricase preparation that is in the tetrameric form generally varies from approximately 20% to 90%. Despite evidence that unPEGylated aggregates of several other proteins are highly immunogenic (see, e.g., Moore, W V, et al., (1980) *J Clin Endocrinol Metab* 51:691-697), previous studies of PEG-uricase do not describe any efforts to limit the content of aggregates, suggesting that the potential immunogenicity of the PEG-modified aggregates was not considered. On the basis of the observations of the present inventors, it appears likely that such aggregates were present in the enzyme preparations used for previous syntheses of PEG-uricase. Their presence may have rendered the task of preparing non-immunogenic conjugates more difficult. It also appears that the large losses of uricolytic activity observed in previous efforts to PEGylate uricase were related to the large number of strands of low molecular weight PEG that were coupled. On the other hand, the methods of uricase purification and PEGylation described herein permit the covalent attachment of as many as 10 strands of PEG per subunit while retaining more than 75% of the uricolytic activity, at least for certain uricases, e.g., pig-baboon chimeric uricase and the enzyme from *A. flavus* (see FIGS. 3A and 4A).

In another preferred embodiment, substantially all aggregates of the tetrameric form of the enzyme may be removed by ion-exchange or size-exclusion chromatography at a pH between about 9 and 10.5, preferably 10.2, prior to PEG conjugation of the resulting substantially tetrameric preparation of uricase. The molecular weight of the uricase in each fraction from the preparative column may be monitored by any size-dependent analytical technique, including, for example, HPLC, conventional size-exclusion chromatography, centrifugation, light scattering, capillary electrophoresis or gel electrophoresis in a non-denaturing buffer. For tetrameric uricase isolated using size-exclusion chromatography, fractions containing only the 140 kDa form of the enzyme may be pooled and used for conjugation to PEG. For tetrameric uricase isolated using ion-exchange chromatography, fractions from the ion-exchange column may be analyzed with respect to size to determine which fractions contain substantial amounts of the tetrameric form without detectable aggregates. Of the uricase thus pooled, at least 90% may be in the tetrameric form; the undesirable aggregates may thus constitute as little as about 10%, 5%, 2%, or less, of the total isolated uricase.

The results presented herein indicate that, even when extensively PEGylated, forms of PBC uricase larger than the tetramer are highly immunogenic in mice (FIG. 12). Furthermore, in mice that had been injected once with PEG conjugates of uricase aggregates, the uricolytic activity in subsequent injections of either PEGylated tetramers or PEGylated aggregates was cleared rapidly from the circulation. In contrast, conjugates prepared from uricase containing less than 5% aggregates could be reinjected many times without any acceleration of their clearance rates (FIG. 7) and without the detectable formation of antibodies, as measured by a sensitive enzyme-linked immunoassay. The use of highly purified tetrameric uricase further distinguishes the improved conjugates of the present invention from the PEG-uricase preparations described previously. In contrast, the presence of a significant proportion (e.g., >10%) of aggregates in the uricase preparations used by some previous investigators may have led them to couple large numbers of strands of PEG in efforts to suppress the immunogenicity. Consequently, the enzymatic activity of the resultant conjugates was decreased substantially. In other embodiments, the present invention expressly contemplates PEGylated uricase in non-tetrameric form, such as, for example, uricase dimers, so long as the preparations of such conjugated uricase retain at least about 75% of their uricolytic activity and are substantially non-immunogenic.

In another embodiment of the present invention, a mutated baboon liver uricase of unexpectedly increased potency, relative to that of the unmutated enzyme, is provided. This improved primate uricase was prepared by conventional recombinant DNA techniques. It was particularly unexpected that the substitution of a single amino acid residue (histidine for tyrosine at position 97) in baboon uricase would result in a substantial increase in specific enzymatic activity. When expressed in $E.$ $coli$, this mutant protein was found to have at least 60% higher specific activity than the recombinant baboon enzyme from which it was derived.

In another embodiment, the specific activity is increased and/or the solubility of the unPEGylated enzyme is improved by expressing truncated variants of porcine or porcine-baboon chimeric uricases from which at least the first six amino acids at the amino terminal and/or at least the last three amino acids at the carboxyl terminal are deleted from the expressed proteins (see FIG. 6). Recombinant uricases with the carboxyl-terminal truncation may have improved solubility prior to PEGylation because of the removal of the peroxisomal targeting sequence. See Miura, S, et al., (1994) $Eur$ $J$ $Biochem$ 223:141-146.

The PEG-uricase conjugates of the present invention are useful for lowering the levels of uric acid in the body fluids and tissues of mammals, preferably humans, and can thus be used for treatment of elevated uric acid levels associated with conditions including gout, tophi, renal insufficiency, organ transplantation and malignant disease. PEG-uricase conjugates may be injected into a mammal having excessive uric acid levels by any of a number of routes, including intravenous, subcutaneous, intradermal, intramuscular and intraperitoneal routes. Alternatively, they may be aerosolized and inhaled. See Patton, J S, (1996) $Adv$ $Drug$ $Delivery$ $Rev$ 19:3-36 and U.S. Pat. No. 5,458,135. The effective dose of PEG-uricase of the present invention will depend on the level of uric acid and the size of the individual. In one embodiment of this aspect of the invention, PEG-uricase is administered in a pharmaceutically acceptable excipient or diluent in an amount ranging from about 10 µg to about 1 g. In a preferred embodiment, the amount administered is between about 100 µg and 500 mg. More preferably, the conjugated uricase is administered in an amount between 1 mg and 100 mg, such as, for example, 5 mg, 20 mg or 50 mg. Masses given for dosage amounts of the embodiments refer to the amount of protein in the conjugate.

Pharmaceutical formulations containing PEG-uricase can be prepared by conventional techniques, e.g., as described in Gennaro, A R (Ed.) (1990) $Remington's$ $Pharmaceutical$ $Sciences$, 18th Edition Easton, Pa.: Mack Publishing Co. Suitable excipients for the preparation of injectable solutions include, for example, phosphate buffered saline, lactated Ringer's solution, water, polyols and glycerol. Pharmaceutical compositions for parenteral injection comprise pharmaceutically acceptable sterile aqueous or non-aqueous liquids, dispersions, suspensions, or emulsions as well as sterile powders for reconstitution into sterile injectable solutions or dispersions just prior to use. These formulations may contain additional components, such as, for example, preservatives, solubilizers, stabilizers, wetting agents, emulsifiers, buffers, antioxidants and diluents.

PEG-uricase may also be provided as controlled-release compositions for implantation into an individual to continually control elevated uric acid levels in body fluids. For example, polylactic acid, polyglycolic acid, regenerated collagen, poly-L-lysine, sodium alginate, gellan gum, chitosan, agarose, multilamellar liposomes and many other conventional depot formulations comprise bioerodible or biodegradable materials that can be formulated with biologically active compositions. These materials, when implanted or injected, gradually break down and release the active material to the surrounding tissue. For example, one method of encapsulating PEG-uricase comprises the method disclosed in U.S. Pat. No. 5,653,974, which is hereby incorporated by reference. The use of bioerodible, biodegradable and other depot formulations is expressly contemplated in the present invention. The use of infusion pumps and matrix entrapment systems for delivery of PEG-uricase is also within the scope of the present invention. PEG-uricase may also advantageously be enclosed in micelles or liposomes. Liposome encapsulation technology is well known in the art. See, e.g., Lasic, D, et al., (Eds.) (1995) $Stealth$ $Liposomes$. Boca Raton, Fla.: CRC Press.

The PEG-uricase pharmaceutical compositions of the invention will decrease the need for hemodialysis in patients at high risk of urate-induced renal failure, e.g., organ transplant recipients (see Venkataseshan, V S, et al., (1990) $Nephron$ 56:317-321) and patients with some malignant diseases. In patients with large accumulations of crystalline urate (tophi), such pharmaceutical compositions will improve the quality of life more rapidly than currently available treatments.

The following examples, which are not to be construed as limiting the invention in any way, illustrate the various aspects disclosed above. These examples describe PEG-uricases prepared by coupling activated (i.e., electrophilic) PEG derivatives of several sizes and compositions with naturally occurring porcine, fungal or bacterial uricases, or with recombinant soybean, porcine or pig-baboon chimeric uricases. Results of activity, solubility, stability, pharmacokinetic, pharmacodynamic and immunological studies are included. The data in FIGS. 8-11 provide evidence of the ability of PEG-modified PBC uricase of this invention to correct hyperuricemia and hyperuricosuria and to preserve renal structure and function in an animal model in which hyperuricemia and hyperuricosuria occur and cause serious renal damage. Wu, X, et al., (1994) $Proc$ $Natl$ $Acad$ $Sci$ $USA$ 91:742-746. These examples provide guidance to one with ordinary skill in the art for producing substantially non-immunogenic conjugates of uricase that retain at least about 75% of the uricolytic activity of the unmodified enzyme.

Example 1

Purification of the Tetrameric Form of Uricase

The tetrameric form of uricase (molecular weight ca. 140 kDa) was purified from a solution of porcine liver uricase by preparative size-exclusion or ion-exchange chromatography, followed by analytical size-exclusion chromatography. Porcine liver uricase was obtained from Sigma-Aldrich, St. Louis, Mo., catalog No. U2350 or U3377; or Boehringer Mannheim, Indianapolis, Ind.

Preparative and analytical size-exclusion chromatography were performed at pH 10-10.5, preferably 10.2, in 10 mM sodium carbonate buffer containing 0.1 M NaCl on Superdex 200 columns that had been previously calibrated with proteins of known molecular weight. Superdex was obtained from Amersham Pharmacia, Piscataway, N.J. Any buffer may be used that is capable of maintaining the desired pH and that is compatible with the chemistry to be used for subsequent PEG coupling. Such buffers are well known in the art. The ultraviolet absorbance of the eluate from the preparative column was monitored at 280 nm, and uricase-containing portions of the eluate corresponding to the molecular weight of the desired tetrameric form, but free of higher molecular weight species, were collected for use in synthesizing substantially non-immunogenic PEG-uricase as described in Example 2. Alternatively, tetrameric forms of uricase can be isolated using other size-exclusion media such as, for example, Superose 12 (Amersham Pharmacia) or any other medium that is compatible with mildly alkaline solutions and that has an appropriate size fractionation range. Such media are readily available and are well known in the art.

Ion-exchange chromatography was performed at pH 10-10.5, preferably 10.2, on Mono Q columns (Amersham Pharmacia, Piscataway, N.J.) that had been equilibrated with 0.1 M sodium carbonate buffer. Any buffer that is compatible with the chemistry of PEG coupling and that is capable of maintaining the desired pH may be used at sufficiently low ionic strength to permit the adsorption of uricase to the column. Such buffers are well known in the art. The ultraviolet absorbance of the eluate was monitored at 280 nm during elution of the uricase from the ion-exchange resin by increasing the ionic strength of the applied buffer solution, e.g. by a linear gradient of 0 to 0.5 M NaCl in the sodium carbonate buffer. Size-exclusion HPLC was then used to identify the fractions of the eluate containing the desired tetrameric form of uricase, without detectable aggregates, for the synthesis of substantially non-immunogenic PEG-uricase. Alternatively, the tetrameric form of uricase can be isolated using other ion-exchange media, such as Q-Sepharose (Amersham Pharmacia) or any other medium that is compatible with mildly alkaline solutions. Such media are readily available and are well known in the art.

Uricase activity was assayed using a modification of standard methods. See, e.g., Fridovich (1965); Nishimura, et al., (1979). Solutions of uric acid were prepared fresh daily in 50 mM sodium borate buffer, pH 9.2, to provide final concentrations in the assay of 6-150 µM. Uricase preparations were diluted in this borate buffer containing bovine serum albumin (Sigma-Aldrich, St. Louis, Mo., catalog No. A-7030), so that the final concentration of albumin in the assay was 0.1 mg/mL. After mixing various dilutions of the enzyme with the substrate in the wells of a microtiter plate in a microplate reader, the rate of disappearance of uric acid at 25° C. was monitored at 292 nm every 4 seconds for 3 minutes. From samples in which between 10% and 40% of the substrate was consumed within 3 minutes, at least 20 data points were used to calculate the maximal rate of decrease in the absorbance per minute. One international unit (IU) of uricase activity is defined as the amount of enzyme that consumes one micromole of uric acid per minute; specific activities are expressed as IU/mg protein. Some of the data for relative uricase activities in FIGS. 1A-5B were obtained using 100 µM uric acid in the assay. Other results for the velocity at 100 µM uric acid ($V_{100}$) were calculated from the values of the Michaelis constant ($K_M$) and the maximal velocity ($V_{max}$) for the respective enzyme preparations, using the formula:

$$V_{100}=100 \times V_{max}/(K_m+100)$$

where $K_M$ is expressed in micromolar units.

Example 2

PEG Coupling to Tetrameric Porcine Uricase

To a solution of tetrameric uricase in 0.1 M sodium carbonate buffer, pH 10.2, 10-200 moles of an activated derivative of monomethoxy PEG, e.g., the 4-nitrophenyl carbonate (NPC-PEG), of various sizes (5 kDa to 30 kDa) were added for each mole of uricase subunit (molecular weight 35 kDa). These and other suitable activated PEGs are available from Shearwater Polymers. Instructions for coupling these PEGs to proteins are given in the catalog of Shearwater Polymers, on the Internet at www.swpolymers.com, and in J M Harris, et al., (Eds.) (1997) *Poly(ethylene glycol) Chemistry and Biological Applications. ACS Symposium Series* 680, Washington, D.C.: American Chemical Society. The coupling reaction was allowed to proceed at 0-8° C. until the extent of PEG coupling no longer changed significantly with time. Unreacted PEG was then removed from the reaction product by chromatography and/or ultrafiltration.

The number of strands of PEG coupled per subunit of uricase was determined by an adaptation of the methods described by Kunitani, M, et al., (1991) *J Chromatogr* 588: 125-137; Saifer, et al., (1997) and Sherman, et al., (1997). Briefly, aliquots of the PEGylation reaction mixtures or fractions from the preparative ion-exchange or size-exclusion columns were characterized by analytical size-exclusion HPLC on a TSK 5,000 $PW_{XL}$ column at room temperature in 10 mM sodium carbonate buffer, pH 10.2, containing 0.1 M NaCl. The HPLC column was obtained from TosoHaas, Montgomeryville, Pa. Proteins and PEGs were monitored by ultraviolet absorbance and refractive index detectors. The amount of protein in the conjugate was calculated from the ultraviolet absorbance relative to that of the appropriate unmodified uricase standard. The amount of PEG in the conjugate was then calculated from the area of the refractive index peak, corrected for the contribution of the protein to refractive index, relative to the area of the refractive index peak of the appropriate PEG standard.

FIG. 2A shows the retention of activity by PEGylated porcine liver uricase as a function of the number of strands of PEG coupled per subunit. Data of the present inventors (▲, □) are compared with those of Chen, et al., (1981). The data point within a large circle denotes a conjugate reported to be non-immunoreactive by Chen, et al., (1981). As shown in FIG. 2A, conjugates of tetrameric porcine uricase with up to 6 strands of 30 kDa PEG per subunit or up to 7 strands of 5 kDa PEG per subunit retained at least 75% of the activity of the unmodified enzyme. The apparent increase in specific activity with an increasing number of strands of 5 kDa or 30 kDa PEG (up to about 4 strands per subunit) may reflect the relative insolubility or instability of the unmodified enzyme compared to the conjugates. As shown in FIG. 2B, conjugates of porcine uricase with an average of more than 3 strands of 30 kDa PEG per subunit contain a greater mass of PEG than was found sufficient to preclude immunoreactivity by Chen, et al., (1981).

Example 3

Properties of PEG Conjugates of Tetrameric Recombinant PBC Uricase

Recombinant pig-baboon chimeric (PBC) uricase cDNA was subcloned into the pET3d expression vector (Novagen, Madison, Wis.) and the resultant plasmid construct was transformed into and expressed in a strain of *Escherichia coli* BL21(DE3)pLysS (Novagen). These procedures were carried out using methods well known in the art of molecular biology.

See Erlich (1989); Sambrook, et al., (1989); Ausubel, F, et al., (Eds.), (1997) *Short Protocols in Molecular Biology*. New York: John Wiley & Sons.

FIG. 6 shows the deduced amino acid sequence of PBC uricase (amino acids 1-225 of SEQ ID NO: 1 and amino acids 226-304 of SEQ ID NO: 2), compared with the porcine (SEQ ID NO: 1) and baboon (SEQ ID NO: 2) sequences. Residues in the baboon sequence that differ from those in the porcine sequence are shown in bold type. The porcine and baboon sequences were first determined by Wu, et al., (1989) and were confirmed by the present inventors. SEQ ID NO. 1 is identical to Accession Number p16164 of GenBank, except for the absence of the initial methionyl residue in the GenBank sequence. SEQ ID NO. 2 is identical to Accession Number p25689 of GenBank, except for the absence of the initial methionyl residue and a change from histidine to threonine at residue 153 in the GenBank sequence (residue 154 in FIG. 6).

The tetrameric form of PBC uricase was isolated and coupled to PEGs of various molecular weights as described in Examples 1 and 2. Conjugates prepared with 5 kDa, 10 kDa, 19 kDa or 30 kDa PEG contained up to 10 strands of PEG per subunit. Those prepared with PEGs of at least 10 kDa retained more than 95% of the initial specific activity of the recombinant uricase (FIGS. 3A-3B).

The following properties of a conjugate of tetrameric PBC uricase with approximately 6 strands of 10 kDa PEG per subunit are illustrated in the indicated figures: the lack of immunogenicity (FIG. 7) and the efficacy in uricase-deficient mice in 1) correcting hyperuricemia and hyperuricosuria (FIG. 8); 2) decreasing the severity of a urine-concentrating defect (FIG. 9), and 3) decreasing the severity of nephrogenic diabetes insipidus (FIG. 10). In addition, this PEG-uricase decreased the severity of uric acid-related renal damage, as visualized by magnetic resonance microscopy (FIG. 11).

FIG. 7 shows the activity of PBC uricase in mouse serum 24 h after each of four or five intraperitoneal injections of PEG-uricase, relative to the value 24 h after the first injection. PEG conjugates were prepared from three different preparations of PBC uricase using two different techniques for PEG activation. One preparation (●) was tested in uricase-deficient (uox −/−) mice; the other two (Δ, ■) were tested in normal BALB/c mice. The most immunoreactive preparation (Δ) was prepared from purified PBC uricase containing an unknown quantity of uricase aggregates coupled to an average of 7 strands of 5 kDa PEG per subunit, using the succinimidyl carbonate derivative of PEG (SC-PEG). Zalipsky, U.S. Pat. No. 5,612,460, hereby incorporated by reference. The moderately immunoreactive preparation (■) was prepared by coupling a PBC uricase preparation containing 11% aggregates to an average of 2 strands of 19 kDa PEG per subunit, using a 4-nitrophenyl carbonate derivative of PEG (NPC-PEG). Sherman, et al., (1997). The least immunoreactive conjugate (●) was prepared by coupling an average of 6 strands of 10 kDa NPC-PEG per subunit to a preparation of PBC uricase containing <5% aggregated uricase.

FIG. 8 shows the inverse relationship between the concentrations of uric acid in the serum and urine and the activity of injected PEG-uricase in the serum of a uricase-deficient (uox −/−) mouse. Injections at zero time and after 72 h contained 0.43 IU of PBC uricase conjugated to an average of 6 strands of 10 kDa PEG per enzyme subunit.

FIG. 9 shows that treatment of uricase-deficient mice with PEG-modified PBC uricase decreased the severity of a urine-concentrating defect. The mean and standard deviation of data for urine osmolality are shown for two mice containing one copy of the normal murine uricase gene (uox +/−), six untreated homozygous uricase-deficient mice (uox −/−) and six homozygous uricase-deficient mice that were injected ten times between the third and 72nd day of life with either 95 or 190 mIU of PEG-uricase. Mice of each genetic background either had received water ad libitum (solid bars) or had been deprived of water for 12 h (hatched bars) prior to collection of their urine.

FIG. 10 shows that treatment of uricase-deficient mice with PEG-modified PBC uricase decreased the severity of nephrogenic diabetes insipidus, characterized by abnormally high consumption of water and abnormally high urine output. The genetic backgrounds of the mice and treatment protocol were the same as in FIG. 9. The mean and standard deviation of the daily water consumption (solid bars) and urine output (hatched bars) are shown for three groups of six mice.

FIG. 11 shows that treatment of uricase-deficient mice with PEG-modified PBC uricase decreased the severity of uric acid-induced nephropathy, as visualized by magnetic resonance microscopy. The genetic backgrounds of the three groups of mice and the treatment protocol were the same as in FIGS. 9 and 10. Magnetic resonance microscopy was performed at the Center for in vivo Microscopy, Duke University Medical Center, Durham, N.C.

In addition to the results summarized in FIGS. 8-11, it was demonstrated that the uric acid levels in the urine of all uricase-deficient mice decreased dramatically after treatment with PEG-modified PBC uricase. Finally, FIG. 12 shows that, unlike the PEG-modified tetrameric form of PBC uricase, the octameric form (molecular weight=280 kDa), even when extensively PEGylated, is immunogenic in mice. This property is reflected in the accelerated clearance of the PEG-modified octamer within 5 days after a single intraperitoneal injection. The same mice were re-injected with the same dose of the same PEG-uricase preparations on days 8 and 15. Twenty-four hours after the second and third injections, uricolytic activity was undetectable in the sera of mice injected with the PEGylated octamer, but was readily detected in the sera of those injected with the PEGylated tetramer. These findings, in combination with the accelerated clearance of the PEGylated octamer observed after the first injection (FIG. 12), support the utility of removing all Mums of uricase larger than the tetramer prior to PEGylation of the enzyme.

Example 4

PEG Conjugation of Uricase From *Candida utilis*

Uricase from *Candida utilis* was obtained from either Sigma-Aldrich (St. Louis, Mo.; catalog No. U1878) or Worthington Biochemical Corporation (Freehold, N.J.; catalog No. URYW). Proceeding as described in Examples 1 and 2, the tetrameric faint was isolated and PEG conjugates were synthesized with 5 kDa, 10 kDa or 30 kDa PEG (FIGS. 1A-1B). FIG. 1A shows the retention of activity by PEGylated uricase from *Candida utilis* as a function of the number of strands of PEG coupled per subunit. Data of the present inventors (▲, ●, □) are compared with those of Nishimura, et al., (1979); Nishimura, et al., (1981); Chen, et al., (1981); Davis, et al., (1981); Tsuji, et al., (1985); Yasuda, et al., (1990), and Fujita, et al., (1991). Data points within large circles denote conjugates reported to be non-antigenic by Nishimura, et al., (1979 or 1981) or non-immunoreactive by Chen, et al., (1981).

FIG. 1B shows the retention of activity by PEGylated uricase from *Candida utilis* as a function of the total mass of PEG coupled per subunit. Data of the present inventors (▲, ●, □) are compared with those of the same reports as in FIG. 1A. Data points within large circles have the same meaning as in FIG. 1A.

As shown in FIGS. 1A and 1B, conjugates with an average of up to 6 strands of 5 kDa or 30 kDa PEG or 9 strands of 10 kDa PEG per subunit retained at least 75% of the activity of the unmodified enzyme. The apparent increase in specific activity as an increasing number of strands of 30 kDa PEG is attached (up to 5 or 6 strands per subunit) may reflect the relative insolubility or instability of the unmodified enzyme compared to the conjugates.

Example 5

PEG Conjugation of Uricase from *Aspergillus flavus*

Uricase from *Aspergillus flavus* was obtained from Sanofi Winthrop (Gentilly Cédex, France). Proceeding as described in Example 2, conjugates with PEGs of various molecular weights were synthesized (FIGS. 4A-4B). Conjugates prepared by coupling the enzyme from *A. flavus* with an average of up to 12 strands of 5 kDa PEG or up to 7 strands of 30 kDa PEG per subunit retained at least 75% of the initial specific activity of this fungal uricase.

Example 6

PEG Conjugation of Soybean Uricase

Recombinant uricase from soybean root nodule (also called nodulin 35) was prepared and purified as described by Kahn and Tipton (Kahn, K, et al., (1997) *Biochemistry* 36:4731-4738), and was provided by Dr. Tipton (University of Missouri, Columbia, Mo.). Proceeding as described in Examples 1 and 2, the tetrameric form was isolated and conjugates were prepared with PEGs of various molecular weights (FIGS. 5A-5B). In contrast to uricase from *Candida utilis* (FIG. 1A), porcine uricase (FIG. 2A), pig-baboon chimeric uricase (FIG. 3A) and uricase from *Aspergillus flavus* (FIG. 4A), the soybean enzyme tolerated coupling of only approximately 2 strands of 5 kDa or 30 kDa PEG per subunit with retention of at least 75% of the initial uricolytic activity.

Example 7

PEG Conjugation of Uricase from *Arthrobacter globiformis*

Uricase from *Arthrobacter globiformis* was obtained from Sigma-Aldrich (catalog No. U7128). See Japanese Patent 9-154581. Proceeding as described in Examples 1 and 2, the tetrameric form was isolated and conjugates with 5 kDa and 30 kDa PEG were prepared. While conjugates with an average of more than 3 strands of 5 kDa PEG per subunit retained less than 60% of the initial specific activity, conjugates with an average of approximately 2 strands of 30 kDa PEG per subunit retained at least 85% of the initial specific activity.

Example 8

PEG Conjugation of Amino-Truncated Porcine and PBC Uricases

Recombinant porcine and PBC uricases from which the first six amino acids at the amino terminal are deleted are expressed in and purified from *E. coli* by standard techniques, as described in Example 3. Proceeding as described in Examples 1 and 2, PEG conjugates of the amino-truncated uricases are synthesized to produce substantially non-immunogenic conjugates that retain at least 75% of the initial specific activity.

Example 9

PEG Conjugation of Porcine and PBC Uricases Truncated at the Carboxyl Terminal or Both the Amino and Carboxyl Terminals Recombinant porcine and PBC uricases from which the last three amino acids at the carboxyl terminal are deleted are expressed in and purified from *E. coli* by standard techniques, as described in Example 3. This carboxyl-terminal deletion may enhance the solubility of the unmodified enzymes, since it removes the peroxisomal-targeting signal. See Miura, et al., (1994). Proceeding as described in Examples 1 and 2, PEG conjugates of the carboxyl-truncated uricases are synthesized to produce substantially non-immunogenic conjugates that retain at least 75% of the initial specific activity. The sequence of recombinant PBC uricase truncated by six residues at the amino terminal and by three residues at the carboxyl terminal (PBC-NT-CT) is shown in FIG. 6. This uricase is expressed, purified and PEGylated as described in Examples 1, 2 and 3 to produce substantially non-immunogenic conjugates that retain at least 75% of the initial specific activity.

Example 10

PEG Conjugation of Porcine Uricase Mutants Containing an Increased Number of PEG Attachment Sites Recombinant porcine uricases are prepared as described in Example 3, in which the potential number of sites of PEG attachment is increased by replacing one or more arginine residues with lysine. See Hershfield, M S, et al., (1991) *Proc Natl Acad Sci USA* 88:7185-7189. The amino acid sequence of one example of such a mutant (PKS uricase), in which the arginine at residue 291 is replaced by lysine and the threonine at residue 301 is replaced by serine, is shown in FIG. 6. Proceeding as described in Examples 1 and 2, PEG is conjugated to this uricase to produce substantially non-immunogenic conjugates that retain at least 75% of the initial specific activity of the recombinant uricase.

Example 11

PEG Conjugation of a Recombinant Baboon Uricase Mutant

Using standard methods of molecular biology, as in Example 3, recombinant baboon uricase is constructed having an amino acid substitution (histidine for tyrosine) at position 97 (see baboon sequence in FIG. 6). Proceeding as described in Examples 1 and 2, PEG conjugates of the tetrameric form of the recombinant baboon uricase mutant are synthesized to produce conjugates of substantially reduced immunogenicity that retain at least 75% of the initial specific activity of the recombinant uricase.

Example 12

Immunogenicity of PEG Conjugates from *Candida utilis, Aspergillus flavus*, and *Arthrobacter globiformis*

Uricase from *Candida utilis, Aspergillus flavus*, and *Arthrobacter globiformis* are obtained as described in Examples 4, 5, and 7, respectively. Proceeding as described in Examples 1 and 2, PEG conjugates are synthesized with 5 kDa, 10 kDa, 20 kDa or 30 kDa PEG. The immunogenicity of these conjugates is substantially reduced or eliminated.

What is claimed is:

1. A method for isolating a tetrameric form of uricase from a solution of purified uricase, said purified uricase comprising tetrameric uricase and uricase aggregates, said method comprising:

separating the solution into fractions on at least one separation column at a pH of 9 to 10.5, wherein said column is selected from the group consisting of an ion-exchange column and a size-exclusion column; and recovering from said column one or more fractions that contain isolated tetrameric uricase, wherein said one or more fractions contain less than 10% of uricase aggregates larger than tetramers.

2. The method of claim 1, wherein said separating is performed at a pH of 10.2.

3. The method of claim 1, wherein said separating is performed at a pH of 10 to 10.5.

4. The method of claim 1, further comprising analyzing said fractions to determine at least one property selected from the group consisting of the presence of said tetrameric uricase and the absence of said uricase aggregates.

5. The method of claim 4, wherein said analyzing comprises at least one analysis selected from the group consisting of chromatography, centrifugation, light scattering and electrophoresis.

6. The method of claim 5, wherein said analyzing comprises high performance liquid chromatography.

* * * * *

UNITED STATES PATENT AND TRADEMARK OFFICE
CERTIFICATE OF CORRECTION

| | |
|---|---|
| PATENT NO. | : 8,067,553 B2 |
| APPLICATION NO. | : 12/769570 |
| DATED | : November 29, 2011 |
| INVENTOR(S) | : Williams et al. |

Page 1 of 1

It is certified that error appears in the above-identified patent and that said Letters Patent is hereby corrected as shown below:

In the Claims

Column 25
Line 37, the first instance of "purified uricase" should be replaced with --purified recombinant mammalian uricase--.

Signed and Sealed this
Sixteenth Day of December, 2014

Michelle K. Lee
*Deputy Director of the United States Patent and Trademark Office*

SEQUENCE LISTING

<160> NUMBER OF SEQ ID NOS: 3

<210> SEQ ID NO 1
<211> LENGTH: 304
<212> TYPE: PRT
<213> ORGANISM: Sus scrofa

<400> SEQUENCE: 1

Met Ala His Tyr Arg Asn Asp Tyr Lys Lys Asn Asp Glu Val Glu Phe
1               5                   10                  15

Val Arg Thr Gly Tyr Gly Lys Asp Met Ile Lys Val Leu His Ile Gln
            20                  25                  30

Arg Asp Gly Lys Tyr His Ser Ile Lys Glu Val Ala Thr Ser Val Gln
        35                  40                  45

Leu Thr Leu Ser Ser Lys Lys Asp Tyr Leu His Gly Asp Asn Ser Asp
    50                  55                  60

Val Ile Pro Thr Asp Thr Ile Lys Asn Thr Val Asn Val Leu Ala Lys
65                  70                  75                  80

Phe Lys Gly Ile Lys Ser Ile Glu Thr Phe Ala Val Thr Ile Cys Glu
                85                  90                  95

His Phe Leu Ser Ser Phe Lys His Val Ile Arg Ala Gln Val Tyr Val
            100                 105                 110

Glu Glu Val Pro Trp Lys Arg Phe Glu Lys Asn Gly Val Lys His Val
        115                 120                 125

His Ala Phe Ile Tyr Thr Pro Thr Gly Thr His Phe Cys Glu Val Glu
    130                 135                 140

Gln Ile Arg Asn Gly Pro Pro Val Ile His Ser Gly Ile Lys Asp Leu
145                 150                 155                 160

Lys Val Leu Lys Thr Thr Gln Ser Gly Phe Glu Gly Phe Ile Lys Asp
                165                 170                 175

Gln Phe Thr Thr Leu Pro Glu Val Lys Asp Arg Cys Phe Ala Thr Gln
            180                 185                 190

Val Tyr Cys Lys Trp Arg Tyr His Gln Gly Arg Asp Val Asp Phe Glu
        195                 200                 205

Ala Thr Trp Asp Thr Val Arg Ser Ile Val Leu Gln Lys Phe Ala Gly
    210                 215                 220

Pro Tyr Asp Lys Gly Glu Tyr Ser Pro Ser Val Gln Lys Thr Leu Tyr
225                 230                 235                 240

Asp Ile Gln Val Leu Thr Leu Gly Gln Val Pro Glu Ile Glu Asp Met
                245                 250                 255

Glu Ile Ser Leu Pro Asn Ile His Tyr Leu Asn Ile Asp Met Ser Lys
            260                 265                 270

Met Gly Leu Ile Asn Lys Glu Glu Val Leu Leu Pro Leu Asp Asn Pro
        275                 280                 285

Tyr Gly Arg Ile Thr Gly Thr Val Lys Arg Lys Leu Thr Ser Arg Leu
    290                 295                 300

<210> SEQ ID NO 2
<211> LENGTH: 304
<212> TYPE: PRT
<213> ORGANISM: Papio hamadryas

<400> SEQUENCE: 2

Met Ala Asp Tyr His Asn Asn Tyr Lys Lys Asn Asp Glu Leu Glu Phe
1               5                   10                  15

-continued

Val Arg Thr Gly Tyr Gly Lys Asp Met Val Lys Val Leu His Ile Gln
                20                  25                  30

Arg Asp Gly Lys Tyr His Ser Ile Lys Glu Val Ala Thr Ser Val Gln
            35                  40                  45

Leu Thr Leu Ser Ser Lys Lys Asp Tyr Leu His Gly Asp Asn Ser Asp
 50                  55                  60

Ile Ile Pro Thr Asp Thr Ile Lys Asn Thr Val His Val Leu Ala Lys
 65                  70                  75                  80

Phe Lys Gly Ile Lys Ser Ile Glu Ala Phe Gly Val Asn Ile Cys Glu
                85                  90                  95

Tyr Phe Leu Ser Ser Phe Asn His Val Ile Arg Ala Gln Val Tyr Val
                100                 105                 110

Glu Glu Ile Pro Trp Lys Arg Leu Glu Lys Asn Gly Val Lys His Val
            115                 120                 125

His Ala Phe Ile His Thr Pro Thr Gly Thr His Phe Cys Glu Val Glu
130                 135                 140

Gln Leu Arg Ser Gly Pro Pro Val Ile His Ser Gly Ile Lys Asp Leu
145                 150                 155                 160

Lys Val Leu Lys Thr Thr Gln Ser Gly Phe Glu Gly Phe Ile Lys Asp
                165                 170                 175

Gln Phe Thr Thr Lys Pro Glu Val Lys Asp Arg Cys Phe Ala Thr Gln
            180                 185                 190

Val Tyr Cys Lys Trp Arg Tyr His Gln Cys Arg Asp Val Asp Phe Glu
            195                 200                 205

Ala Thr Trp Gly Thr Ile Arg Asp Leu Val Leu Glu Lys Phe Ala Gly
210                 215                 220

Pro Tyr Asp Lys Gly Glu Tyr Ser Pro Ser Val Gln Lys Thr Leu Tyr
225                 230                 235                 240

Asp Ile Gln Val Leu Ser Leu Ser Arg Val Pro Glu Ile Glu Asp Met
                245                 250                 255

Glu Ile Ser Leu Pro Asn Ile His Tyr Phe Asn Ile Asp Met Ser Lys
            260                 265                 270

Met Gly Leu Ile Asn Lys Glu Glu Val Leu Leu Pro Leu Asp Asn Pro
            275                 280                 285

Tyr Gly Lys Ile Thr Gly Thr Val Lys Arg Lys Leu Ser Ser Arg Leu
290                 295                 300

<210> SEQ ID NO 3
<211> LENGTH: 304
<212> TYPE: PRT
<213> ORGANISM: Mutant combination of Sus scrofa & Papio hamadryas

<400> SEQUENCE: 3

Met Ala His Tyr Arg Asn Asp Tyr Lys Lys Asn Asp Glu Val Glu Phe
 1               5                  10                  15

Val Arg Thr Gly Tyr Gly Lys Asp Met Ile Lys Val Leu His Ile Gln
                20                  25                  30

Arg Asp Gly Lys Tyr His Ser Ile Lys Glu Val Ala Thr Ser Val Gln
            35                  40                  45

Leu Thr Leu Ser Ser Lys Lys Asp Tyr Leu His Gly Asp Asn Ser Asp
 50                  55                  60

Val Ile Pro Thr Asp Thr Ile Lys Asn Thr Val Asn Val Leu Ala Lys
 65                  70                  75                  80

Phe Lys Gly Ile Lys Ser Ile Glu Thr Phe Ala Val Thr Ile Cys Glu
                85                  90                  95

-continued

```
His Phe Leu Ser Ser Phe Lys His Val Ile Arg Ala Gln Val Tyr Val
            100                 105                 110

Glu Glu Val Pro Trp Lys Arg Phe Glu Lys Asn Gly Val Lys His Val
            115                 120                 125

His Ala Phe Ile Tyr Thr Pro Thr Gly Thr His Phe Cys Glu Val Glu
            130                 135                 140

Gln Ile Arg Asn Gly Pro Pro Val Ile His Ser Gly Ile Lys Asp Leu
145                 150                 155                 160

Lys Val Leu Lys Thr Thr Gln Ser Gly Phe Glu Gly Phe Ile Lys Asp
                165                 170                 175

Gln Phe Thr Thr Leu Pro Glu Val Lys Asp Arg Cys Phe Ala Thr Gln
                180                 185                 190

Val Tyr Cys Lys Trp Arg Tyr His Gln Gly Arg Asp Val Asp Phe Glu
            195                 200                 205

Ala Thr Trp Asp Thr Val Arg Ser Ile Val Leu Gln Lys Phe Ala Gly
            210                 215                 220

Pro Tyr Asp Lys Gly Glu Tyr Ser Pro Ser Val Gln Lys Thr Leu Tyr
225                 230                 235                 240

Asp Ile Gln Val Leu Thr Leu Gly Gln Val Pro Glu Ile Glu Asp Met
                245                 250                 255

Glu Ile Ser Leu Pro Asn Ile His Tyr Leu Asn Ile Asp Met Ser Lys
            260                 265                 270

Met Gly Leu Ile Asn Lys Glu Glu Val Leu Leu Pro Leu Asp Asn Pro
        275                 280                 285

Tyr Gly Lys Ile Thr Gly Thr Val Lys Arg Lys Leu Ser Ser Arg Leu
        290                 295                 300
```